United States Patent
Stoddart et al.

(10) Patent No.: US 9,290,495 B2
(45) Date of Patent: Mar. 22, 2016

(54) TETRACATIONIC CYCLOPHANES AND THEIR USE IN THE SEQUESTRATION OF POLYAROMATIC HYDROCARBONS BY WAY OF COMPLEXATION

(71) Applicant: Northwestern University, Evanston, IL (US)

(72) Inventors: J. Fraser Stoddart, Evanston, IL (US); Jonathan C. Barnes, Waltham, MA (US); Michal Juríček, Basel (CH)

(73) Assignee: Northwestern University, Evanston, IL (US)

( * ) Notice: Subject to any disclaimer, the term of this patent is extended or adjusted under 35 U.S.C. 154(b) by 6 days.

(21) Appl. No.: 14/136,870

(22) Filed: Dec. 20, 2013

(65) Prior Publication Data

US 2014/0179017 A1    Jun. 26, 2014

Related U.S. Application Data

(60) Provisional application No. 61/740,958, filed on Dec. 21, 2012.

(51) Int. Cl.
| | | |
|---|---|---|
| *C07D 471/22* | (2006.01) | |
| *B01D 15/38* | (2006.01) | |
| *B01D 53/02* | (2006.01) | |
| *C01B 31/04* | (2006.01) | |
| *C10G 25/00* | (2006.01) | |
| *C02F 1/68* | (2006.01) | |

(52) U.S. Cl.
CPC .............. *C07D 471/22* (2013.01); *B01D 15/38* (2013.01); *B01D 53/02* (2013.01); *C01B 31/0469* (2013.01); *C01B 31/0484* (2013.01); *C10G 25/003* (2013.01); *B01D 2253/20* (2013.01); *B01D 2253/25* (2013.01); *B01D 2257/7027* (2013.01); *C01B 2204/02* (2013.01); *C02F 1/683* (2013.01); *C10G 2300/1096* (2013.01); *Y10T 436/212* (2015.01)

(58) Field of Classification Search
None
See application file for complete search history.

(56) References Cited

U.S. PATENT DOCUMENTS

| | | |
|---|---|---|
| 5,190,663 A | 3/1993 | Fetzer |
| 5,425,881 A | 6/1995 | Szejtli et al. |
| 6,459,011 B1 | 10/2002 | Tarr et al. |
| 6,787,038 B2 | 9/2004 | Brusseau et al. |

FOREIGN PATENT DOCUMENTS

| | | |
|---|---|---|
| EP | 0623557 | 11/1994 |
| JP | H02225584 A | 9/1990 |
| JP | H02227137 A | 9/1990 |
| JP | 2005220116 A | 8/2005 |

OTHER PUBLICATIONS

International Search Report and Written Opinion issued in PCT/US2013/077144, Apr. 29, 2014.
Barnes et al., ExBox: A Polycyclic Aromatic Hydrocarbon Scavenger, Journal of the American Chemical Society, vol. 135, No. 1, Aug. 28, 2012, pp. 183-192.

*Primary Examiner* — Noble Jarrell
(74) *Attorney, Agent, or Firm* — Bell & Manning, LLC

(57) ABSTRACT

Novel tetracationic cyclophanes incorporating π-electron poor organic compounds into their ring structures, as well as methods of making the cyclophanes, are provided. The cyclophanes are able to form electron donor-acceptor complexes with a variety of polyaromatic hydrocarbons (PAHs) ranging in size, shape, and electron density. Also provided are methods of using the cyclophanes in the sequestration of PAHs in liquid or gaseous samples, the separation of PAHs from liquid or gaseous samples, the detection of PAHs in liquid samples, and the exfoliation of graphene via pseudopolyrotaxane formation.

19 Claims, 9 Drawing Sheets

| 1:1 complex | π-electron count[a] | $K_a/10^3(M^{-1})$ | $\Delta H$ (kcal mol⁻¹) | $\Delta S$ (cal mol⁻¹ K⁻¹) | $\Delta G$ (kcal mol⁻¹) | $\delta$(ppm)[b] |
|---|---|---|---|---|---|---|
| 1 | 10 | 0.286 ± 0.011[c] | — | — | −3.35 ± 0.022 | 7.86 |
| 2 | 14 | 0.883 ± 0.11[c] | — | — | −4.01 ± 0.073 | 7.38 |
| 3 | 14 | 1.38 ± 0.016[d] | −5.72 ± 0.024 | −4.83 ± 0.084 | −4.28 ± 0.0068 | 7.26 |
| 4 | 16 | 7.16 ± 0.50[d,e] | −5.84 ± 0.076 | −1.97 ± 0.29 | −5.25 ± 0.041 | 6.76 |
| 5 | 18 | —[f] | — | — | — | —[g] |
| 6 | 18 | 0.914 ± 0.010[d] | −5.79 ± 0.028 | −5.91 ± 0.096 | −4.03 ± 0.0065 | 7.19 |
| 7 | 18 | 2.32 ± 0.15[c] | — | — | −4.59 ± 0.038 | 7.10 |
| 8 | 18 | 5.71 ± 0.054[d] | −7.66 ± 0.018 | −8.52 ± 0.063 | −5.12 ± 0.0056 | 6.93 |
| 9 | 18 | 19.7 ± 5.0[c] | — | — | −5.85 ± 0.15 | 6.91 |
| 10 | 20 | 88.1 ± 67[c] | — | — | −6.74 ± 0.45 | 6.90 |
| 11 | 24 | —[f] | — | — | — | 5.40 |

[a]Number of π-electrons in the PAH aromatic system. [b]Chemical shifts of the $H_\gamma$-protons of the 1:1 complex. [c]Determined by ¹H NMR spectroscopy. [d]Determined by ITC. [e]Binding constant determined by ¹H NMR spectroscopy for complex 4 is 10.1 ± 1.1 × 10³ M⁻¹. [f]Binding parameters of these complexes could not be determined by either ITC or NMR spectroscopy on account of solubility restrictions. [g]Chemical shift of the $H_\gamma$-protons of this complex could not be determined because of solubility restrictions.

FIG. 7

TETRACATIONIC CYCLOPHANES AND THEIR USE IN THE SEQUESTRATION OF POLYAROMATIC HYDROCARBONS BY WAY OF COMPLEXATION

CROSS-REFERENCE TO RELATED APPLICATIONS

The present application claims priority to U.S. Provisional Patent Application No. 61/740,958 that was filed Dec. 21, 2012, the entire contents of which is hereby incorporated by reference.

REFERENCE TO GOVERNMENT RIGHTS

This invention was made with government support under W911NF-10-1-0510 awarded by the Army Research Office; HDTRA1-08-1-0041 awarded by the Defense Threat Reduction Agency; DE-SC0000989 and DE-SC0005462 awarded by the Department of Energy; CHE0924620 and DMR0520513 awarded by the National Science Foundation; and R01 CA133697 and U54 CA151880 awarded by the National Institutes of Health. The government has certain rights in the invention.

BACKGROUND

PAHs, also known as polyaromatic hydrocarbons, which are composed of fused aromatic rings that do not contain heteroatoms, are an important class of compounds.

PAHs can be found naturally in oil, coal, and tar. They are produced as byproducts in combustion processes of fuel, be it fossil fuel or biomass. Being lipophilic, meaning they mix more easily with oil than water, PAHs dispersed into the environment are primarily deposited in soil, sediment, and oily substances, as particulate matter suspended in air, and in water. As a pollutant, they are of concern because some of the smaller (partially water-soluble) PAHs, such as benzo[a]pyrene, have been identified as carcinogenic, mutagenic, and teratogenic, and they are widely believed to make a substantial contribution to the overall burden of cancer in humans. A major route of exposure to PAHs for people is consumption of food, which can be contaminated from environmental sources as well as industrial or home food processing.

Considering the potential health risks associated with the release of PAHs into the environment, it is of fundamental importance to be able to detect and sequester these harmful molecules. To date, cyclodextrins (CDs) have been used most often to isolate PAHs from crude mixtures, although more recently derivatives of calix[n]arenes, cholic acid, and metalligand diazapyrenium-based metallocycles have been explored as potential suitors for PAHs of different shapes and sizes. It should be noted, however, that the metallocycles described by Quintela et al. incorporate heavy Pd and Pt ligand-metal coordination in order to form supramolecular architectures, which are expensive and would not be ideal from environmental and economical perspectives.

SUMMARY

Tetracationic cyclophanes incorporating π-electron poor organic compounds into their ring structures are provided. Also provided are methods of making and using the novel cyclophanes.

The cyclophanes are characterized by a closed ring structure comprising either two 4,4'-(1,4-phenylene)bispyridinium units and two p-phenylene connected via four methylene bridges or two 4,4'-(4,4'-[n]phenylene)bispyridinium (n≥1) units and two p-phenylene units connected via four methylene bridges. Thus, the cyclophanes can be characterized by formula I:

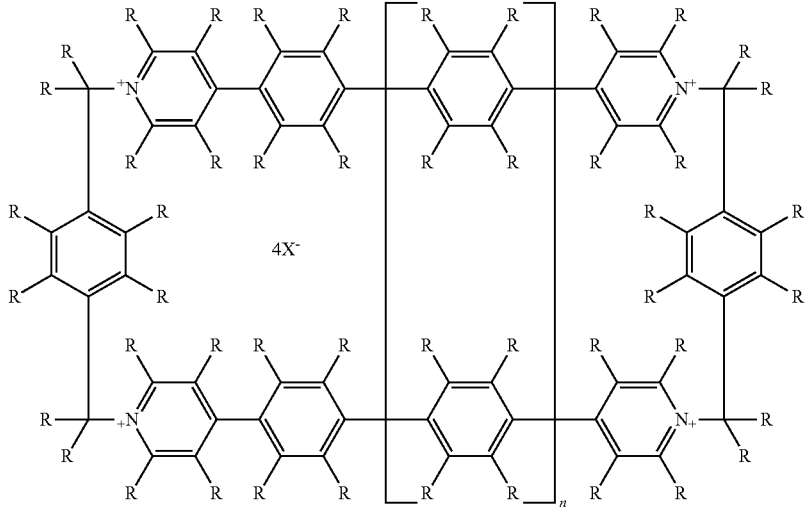

wherein n≥0; R is independently selected from the group consisting of H, alkyl groups, alkenyl groups, alkynyl groups, aryl groups, OH, $NH_2$, SH, F, Cl, Br, I, $P(R_1)_2$, CHO, $COOR_1$, COOM, $CH_2OR_1$, $CH_2OM$, $OR_1$, $NHCOR_1$, $CONHR_1$, CONHM, $CON(R_1)_2$, $N_3$, $NO_2$, $B(OR_1)_2$, $B(OM)_2$, CN, $N(R_1)^{3+}$, $P(R_1)^{3+}$, $PO(R_1)_2$, and OM, where $R_1$ is independently selected from the group consisting of H, alkyl groups, alkenyl groups, alkynyl groups, and aryl groups and M is independently selected from the group consisting of Li, Na, K, Rb and Cs; and $X^-$ is an organic or inorganic negatively charged ion. Specific embodiments of the cyclophanes include those in which n=0 and n=1. In some embodiments, all of the R groups of the cyclophane are H atoms.

One embodiment of a method of making a cyclophane comprises reacting an extended bypyridine with α,α' dibromo-p-xylene to form a bromide salt of the extended bypyridine; converting the bromide salt into its hexafluorophosphate salt; and reacting the hexafluorophosphate salt with another molecule of the extended bipyridine to form the cyclophane. The step of reacting the hexafluorophosphate salt with the extended bipyridine may be done in the presence of a polyaromatic templating compound.

The cyclophanes can be used in methods for sequestering polyaromatic hydrocarbons from samples comprising such polyaromatic hydrocarbons. One such method comprises mixing one or more cyclophanes with the sample, whereby the polyaromatic hydrocarbons form an inclusion complex with the cyclophanes. The inclusion complexes can then be removed from the sample and the complexed polyaromatic hydrocarbons subsequently separated from the cyclophanes. The sequestration may be carried out in organic or aqueous media. In some embodiments, the sample is a vapor phase sample.

The cyclophanes can be used in methods for the chromatographic separation of polyaromatic hydrocarbons from samples comprising mixtures of polyaromatic hydrocarbons. One such method comprises passing the sample over a solid support material on which one or more cyclophanes are immobilized, whereby the polyaromatic hydrocarbons undergo reversible electron donor-acceptor complexation and dissociation interactions with the polyaromatic hydrocarbons, such that different types of the polyaromatic hydrocarbons are separated from one another as they pass over the solid support material.

The cyclophanes can be used in methods for detecting the presence of polyaromatic hydrocarbons in samples comprising polyaromatic hydrocarbons. One such method comprises mixing one or more cyclophanes with the sample, whereby the polyaromatic hydrocarbons form inclusion complexes with the cyclophanes and produce a visible color change in the sample; and monitoring the color change.

The cyclophanes can be used in methods for exfoliating individual graphene nanoribbon sheets from a stack of graphene nanoribbons. One such method comprises exposing the multi-layered graphene nanoribbon stack to a solution comprising one or more cyclophanes, whereby the cyclophanes form polypseudorotaxanes with the graphene nanoribbons which results in the exfoliation of individual nanoribbons as the result of Coulombic repulsion between the cyclophanes. The step of exposing the multi-layered graphene nanoribbon stack to the cyclophanes can comprise synthesizing the graphene nanoribbon stack in the presence of the cyclophanes. Alternatively, the step of exposing the multi-layered graphene nanoribbon stack to the cyclophanes can comprise adding the cyclophanes to a solution comprising the graphene nanoribbon stack, and agitating the solution.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 6(A) Top view of ExBox•4PF$_6$.

FIG. 7. Table of Binding Parameters and H$_γ$-Proton Shifts of the 1:1 ExBox$^{4+}$ ⊂ PAH Complexes 1-11 of the examples.

DETAILED DESCRIPTION

Figure 1:
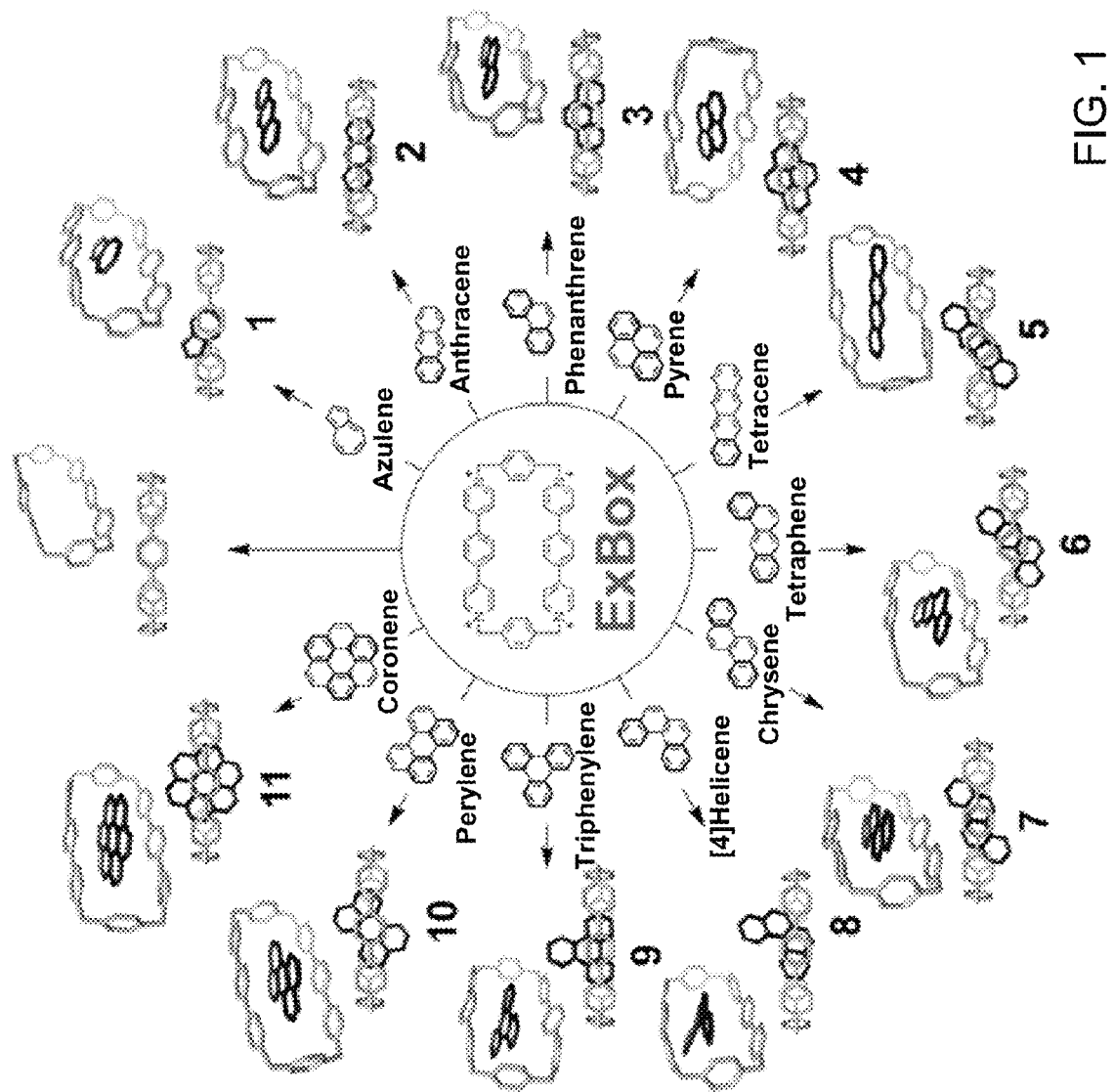
FIG. 1. Single crystal X-ray diffraction (XRD) data obtained for all 11 of the inclusion complexes of ExBox ⊂ Guest•4PF$_6$ (1-11) in Example 1, along with that of ExBox•4PF$_6$ alone (top). The counterions and solvent molecules are removed for the sake of clarity. The structural formulas depicted with bolded π-bonds highlight the Clar's sextet in each π-electron-rich guest.
Figure 2A:
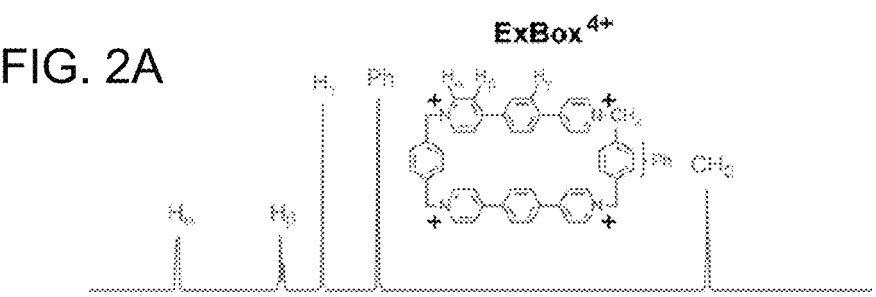
FIG. 2. Aromatic-region insets of the $^1$H NMR spectra of ExBox•4PF$_6$ (A) and its 1:1 complexes with azulene (B), phenanthrene (C), pyrene (D), perylene (E), and coronene (F) recorded in CD$_3$CN at 298 K on a 500 MHz instrument. Downfield shifts of the β and γ protons of ExBox$^{4+}$ as well as upfield shifts of the phenylene protons of ExBox$^{4+}$ are evident. Both downfield and upfield shifts increase as the size of the PAH core becomes larger and larger, indicating the binding of a PAH molecule inside ExBox$^{4+}$ in solution.
Figure 2B:
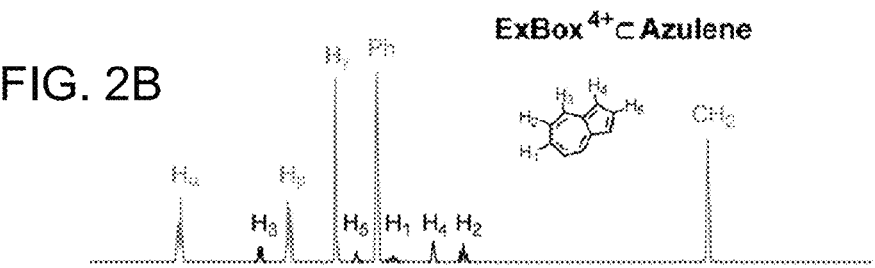
Figure 2C:
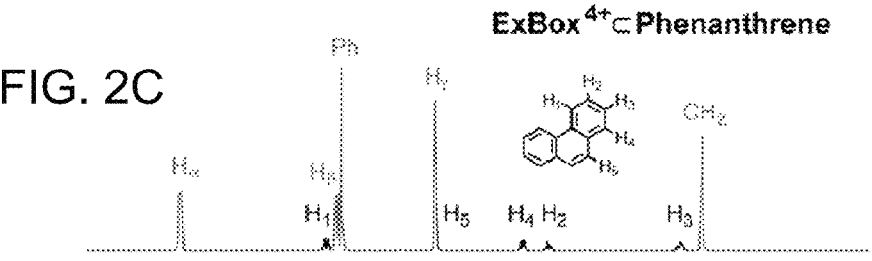
Figure 2D:
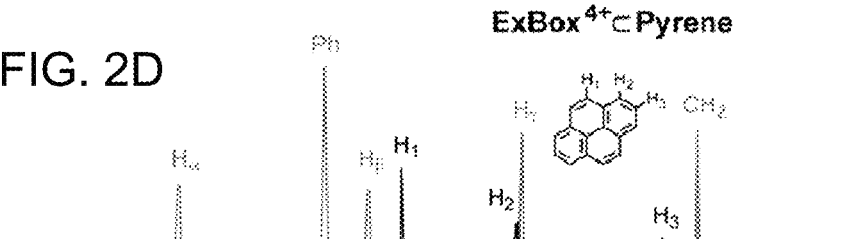
Figure 2E:
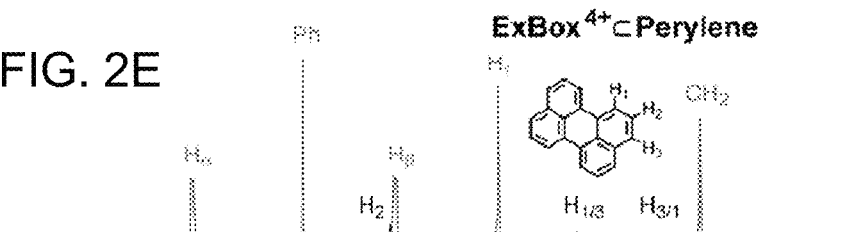
Figure 2F:
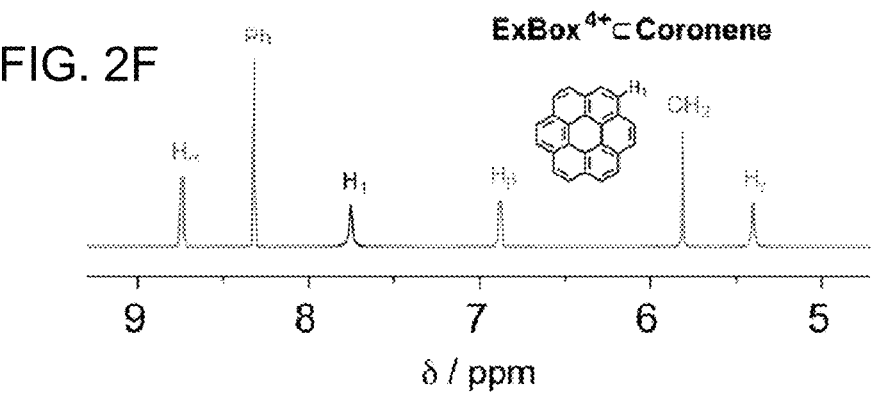

Novel tetracationic cyclophanes incorporating π-electron poor organic compounds into their ring structures are provided. The cyclophanes are able to form inclusion complexes (also referred to as host-guest complexes) via electron donor-acceptor interactions with a variety of PAHs ranging in size, shape, and electron density. As a result, the cyclophanes are useful in a broad range of applications, including the sequestration of PAHs in liquid or gaseous samples, the separation of PAHs from liquid or gaseous samples, the detection of PAHs in liquid samples, and the exfoliation of graphene via pseudopolyrotaxane formation. Also provided are methods of making the novel cyclophanes.

Incorporating π-electron poor organic compounds into rigid cyclophanes allows for a particularly strong affinity between the cyclophanes and the PAHs with which they complex by way of host-guest complexation. Without intending to be bound to any particular theory of the invention, the inventors believe this is a result of fixed π-π (stacking distances and increased charge-transfer interactions that occur when two of the π-electron poor compounds incorporated into a cyclophane sandwich a π-electron rich PAH compound inside the rigid cyclophane ring structure. Additionally, the solubility of the charged organic-based cyclophanes can be tuned to suit different media simply by choosing the appropriate counterion, allowing the host-guest complexation between the π-electron rich guest (donor) and the π-electron poor host (acceptor) to occur in either organic or aqueous media.

The cyclophanes are characterized by formula I:

In other embodiments, at least some of the R groups in formula I represent substituents other than hydrogen atoms. In such embodiments, the R groups are independently selected from the group consisting of H, alkyl groups, alkenyl groups, alkynyl groups, aryl groups, alkoxy groups, OH, $NH_2$, SH, F, Cl, Br, I, $P(R_1)_2$, CHO, $COOR_1$, COOM, $CH_2OR_1$, $CH_2OM$, $OR_1$, $NHCOR_1$, $CONHR_1$, CONHM, $CON(R_1)_2$, $N_3$, $NO_2$, $B(OR_1)_2$, $B(OM)_2$, CN, $N(R_1)^{3+}$, $P(R_1)^{3+}$, $PO(R_1)_2$, and OM, where $R_1$ is independently selected from the group consisting of H, alkyl groups, alkenyl groups, alkynyl groups, and aryl groups and M is independently selected from the group consisting of Li, Na, K, Rb and Cs.

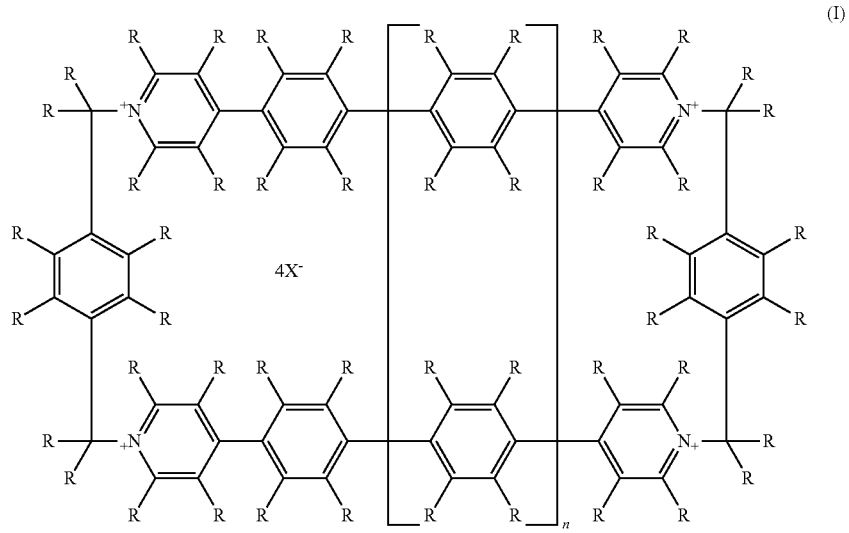

(I)

where n≥0 and $X^-$ is an organic or inorganic anion. Cyclophanes of formula I are denoted "Ex″Box($R_m$)•4X". Thus, the tetracationic cyclophanes, which can bind PAHs ranging in size, shape, and electron density in both organic and aqueous media are constructed from two 4,4'-(4,4'-[n]phenylene)bispyridinium units (also referred to as extended viologens) and two p-phenylene units held together by four methylene bridges. The proposed chemical name is cyclobis(4,4'-(4,4'-[n]phenylene)bispyridin-1-ium-1,4-phenylenebis(methylene))tetrakis(anion), where the anion can be any organic or inorganic negatively charged ion.

In some embodiments, the aromatic rings of the cyclophane are unsubstituted. That is, is some embodiments each of the R groups in formula I is an H atom. In such embodiments, the cyclophanes are characterized by formula II:

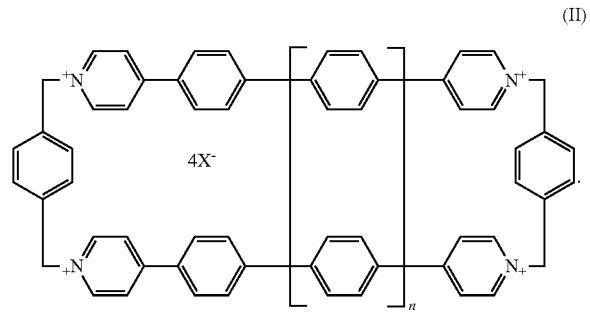

(II)

Cyclophanes of formula II are denoted "Ex″Box•4X".

The alkyl groups may be straight chain (linear), branched or cyclic alkyl groups, including $C_1$-$C_8$ alkyl groups that is, alkyl groups having 1-8 carbon atoms. The alkyl groups may be saturated or unsaturated. The alkenyl groups are hydrocarbon groups having one or more carbon-carbon double bonds and may be linear, branched or cyclic alkenyl groups, including $C_2$-$C_8$ alkenyl groups. The alkynyl groups are hydrocarbon groups having one or more carbon-carbon triple bonds and may be linear or branched alkynyl groups, including $C_2$-$C_8$ alkynyl groups. The alkoxy groups may be linear or branched alkoxy groups, including $C_1$-$C_8$ alkoxy groups. The aryl groups are carbocyclic aromatic groups, including $C_6$-$C_{10}$ aryl groups. The aryl groups may be aralkyl groups in which an alkyl group is itself substituted by an aryl group. The presence of a charged (+1) substituent increases the overall charge by one (i.e., in the case of one charged (+1) substituent, the overall charge is +5), resulting in the increase of the number of counterions, X, needed to balance the positive charge. The presence of a charged (−1) substituent decreases the overall charge by one (i.e., in the case of one charged (−1) substituent, the overall charge is +3), resulting in the decrease of the number of counterions, X, needed to balance the positive charge.

The various R groups recited in the preceding paragraph may themselves be substituted or unsubstitued. For example, R groups comprising substituted functional groups falling into the categories listed above include the following aliphatic derivatives:

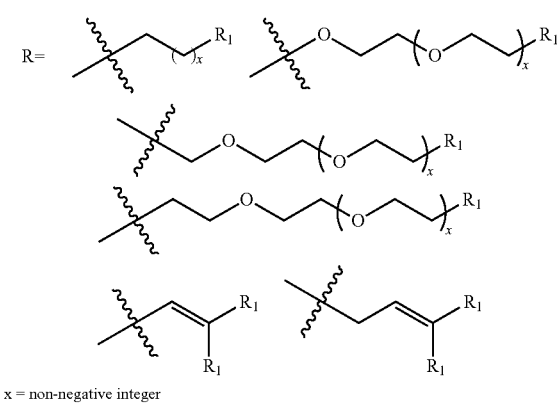

x = non-negative integer where x is a non-negative integer and $R_1$ can be any combination of one or more of the R groups listed in the preceding paragraph. Other R groups comprising substituted functional groups falling into the categories listed above include any combination of one or more of the following aryl derivatives:

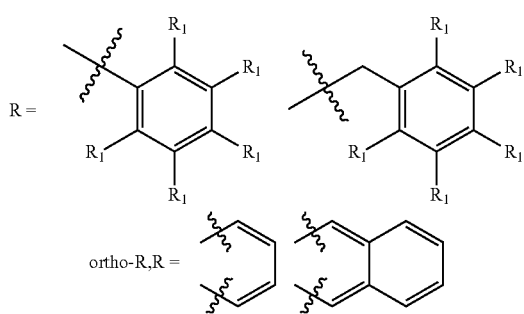

where $R_1$ can be any combination of one or more of the R groups listed in the preceding paragraph.

In some embodiments of the cyclophanes of formula I, n=0. The formula for such cyclophanes is represented by formula III:

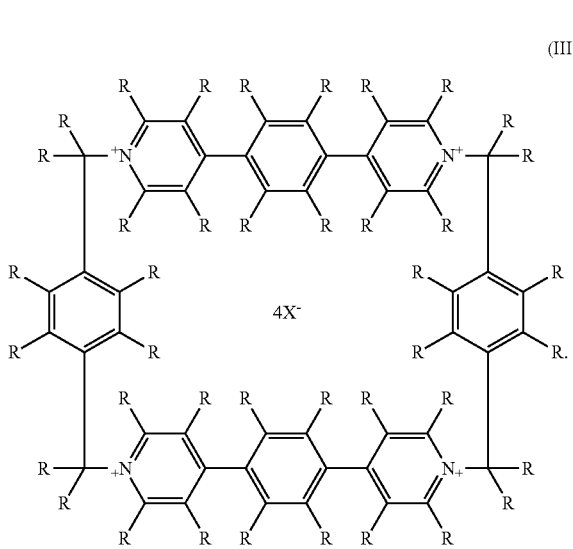

Cyclophanes of formula III are denoted "ExBox($R_m$)•4X".

In some such embodiments, each of the R groups is an H atom. The formula for such cyclophanes is represented by formula IV:

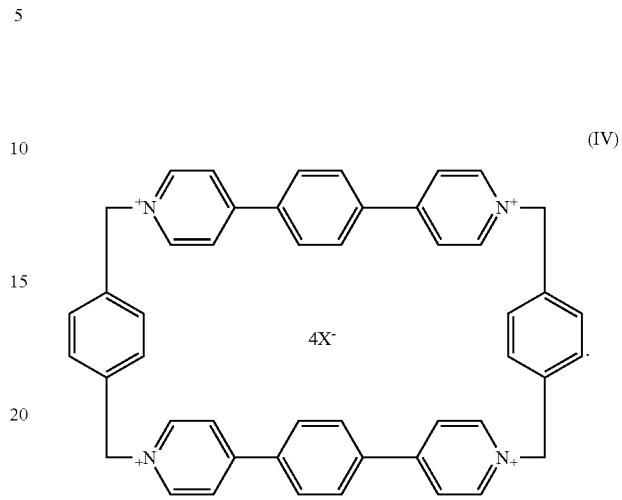

Cyclophanes of formula IV, which are denoted "ExBox•4X", are constructed from two 4,4'-(1,4-phenylene)bispyridinium units and two p-phenylene units held together by four methylene bridges. The proposed chemical name is cyclobis(4,4'-(1,4-phenylene)bispyridin-1-ium-1,4-phenylenebis(methylene))tetrakis(anion), where the anion can be any organic or inorganic negatively charged ion.

In some embodiments of the cyclophanes of formula I, n=1. The formula for such cyclophanes is represented by formula V:

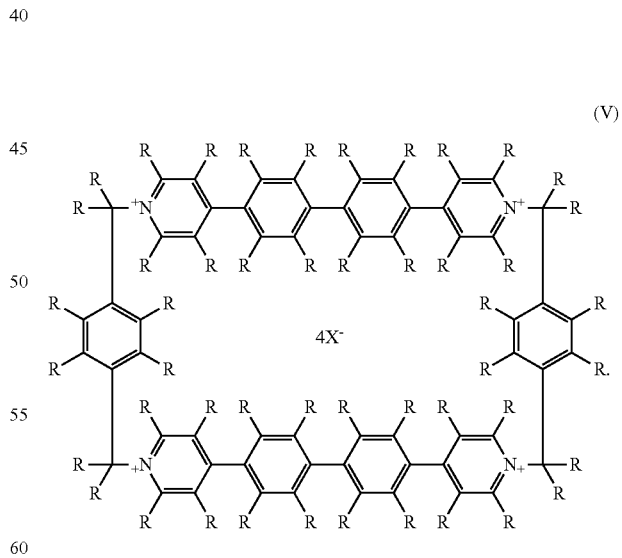

Cyclophanes of formula V are denoted "Ex²Box($R_m$)•4X".

In some such embodiments, each of the R groups is an H atom. The formula for such cyclophanes is represented by formula VI:

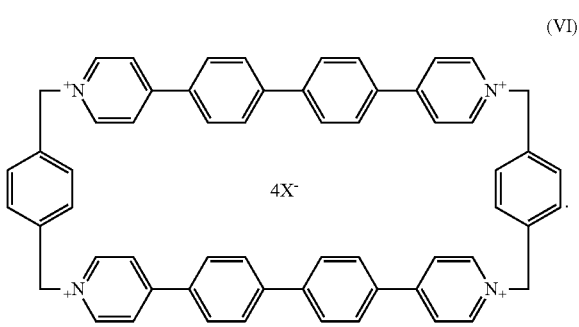 [SMILES: c1cc2ccc1C[n+]1ccc(cc1)-c1ccc(cc1)-c1ccc(cc1)-c1cc[n+](cc1)Cc1ccc(cc1)C[n+]1ccc(cc1)-c1ccc(cc1)-c1ccc(cc1)-c1cc[n+](cc1)C2]

(VI)

Cyclophanes of formula VI, which are denoted "Ex²Box•4X", are constructed from two 4,4'-(4,4'-biphenylene)bispyridinium units and two p-phenylene units held together by four methylene bridges. The proposed chemical name is cyclobis(4,4'-(4,4'-biphenylene)bispyridin-1-ium-1, 4-phenylenebis(methylene))tetrakis(anion), where the anion can be any organic or inorganic negatively charged ion.

PAHs that are able to form electron donor-acceptor inclusion complexes with the present cyclophanes include, but are not limited to, those having from 2 to 7 fused aromatic rings. A few examples of PAH molecules which can be bound by cyclophanes, such as ExBox•4X and its derivatives, are:

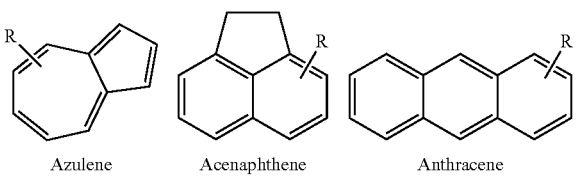

Azulene    Acenaphthene    Anthracene

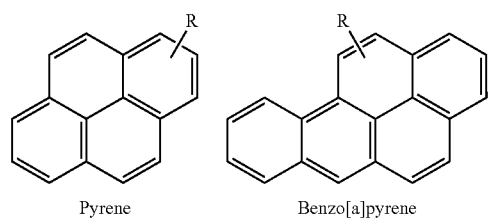

Pyrene    Benzo[a]pyrene where each ring of the PAH can contain any combination of one or more of the following R groups: H atoms, alkyl groups, alkenyl groups, alkynyl groups, and aryl groups. The alkyl groups may be straight chain (linear), branched or cyclic alkyl groups, including $C_1$-$C_8$ alkyl groups that is, alkyl groups having 1-8 carbon atoms. The alkyl groups may be saturated or unsaturated. The alkenyl groups are hydrocarbon groups having one or more carbon-carbon double bonds and may be linear, branched or cyclic alkenyl groups, including $C_2$-$C_8$ alkenyl groups. The alkynyl groups are hydrocarbon groups having one or more carbon-carbon triple bonds and may be linear or branched alkynyl groups, including $C_2$-$C_8$ alkynyl groups. The aryl groups are carbocyclic aromatic group, including $C_6$-$C_{10}$ aryl groups. The names given above correspond to the PAH when R═H. Other examples of PAH molecules that may be complexed by the cyclophanes include phenanthrene, tetracene, tetraphene, chrysene, helicene, triphenylene, perylene and coronene. The structures for each or these PAH molecules is shown in FIG. 1.

Because they form complexes with PAHs, the cyclophanes can be used to sequester PAHs in samples comprising PAHs. Methods of sequestering PAHs using the cyclophanes comprise the steps of mixing one or more of the cyclophanes with the sample, whereby the PAH molecules complex with the cyclophanes via electron donor-acceptor interactions, thereby trapping the PAHs. Once sequestered, the PAHs and cyclophanes can be recovered from the sample and separated. Because the solubility of the cyclophanes can be tuned by the selection of the counterion, the sequestration can take place in either organic media or aqueous media, as well as in biphasic systems comprised of two or more layers of non-miscible phases. Examples of organic media include organic solvents and liquid hydrocarbons, such as crude oil. Examples of aqueous media include water obtained from a natural body of water, such as a pond, river, lake, sea or ocean, or from a supply of drinking water, such as tap water or well water. In some embodiments, the sample comprising the PAH molecules is a vapor phase sample. Examples of vapor phase samples include the gaseous exhaust streams from transportation vehicles or industrial facilities, such as industrial manufacturing or power plants. Other examples include air samples comprising cigarette smoke. In embodiments of the methods in which the cyclophanes are used to sequester PAHs from a vapor phase sample, the cyclophanes may be loaded onto (e.g., coated onto, bonded to and/or impregnated within) a solid support substrate such as a porous composite (e.g., an inorganic composite or ceramic) or a silica gel.

The cyclophanes are also useful in the chromatographic separation of PAH molecules in a sample (organic or aqueous; liquid or vapor) comprising more than one type of PAH. Methods of using the cyclophanes in such chromatographic separations include the steps of passing the sample over a solid support material on which one or more of the cyclophanes are immobilized, wherein the polyaromatic hydrocarbons undergo reversible electron donor-acceptor complexation and dissociation interactions with the PAHs. In this process, the stability of the complexes formed will depend on the precise nature of each PAH and, therefore, the different types of PAHs will be separated from one another as they pass over the solid support material. For example, in some embodiments, a functionalized ExBox•4X or Ex″Box•4X (n≥2) derivative could be tethered or cross-linked to a solid surface—e.g., silica nanoparticles, silica gel, resin, polymer backbones, gels, inorganic architectures, metal organic frameworks, coordination polymers, charcoal, etc.—and used as a chromatographic material, or the active component in a liquid/gas filter.

Notably, as described in greater detail in the examples that follow, at least some embodiments of the cyclophanes undergo a detectible color change when they complex with a PAH molecule in solution. Thus, the cyclophanes find additional utility in the detection of PAH molecules in solution. Methods of using the cyclophanes to detect the presence of PAHs in solution comprise the steps of mixing one or more of the cyclophanes in the solution, whereby the PAHs complex with the cyclophanes, producing a visible color change in the solution; and detecting or monitoring the color change over time.

The ability to form complexes with PAH molecules also makes the cyclophanes useful in the exfoliation of multi-sheet graphene materials, such as stacked graphene nanoribbons. As used herein, the term graphene nanoribbon refers to a sheet of graphene that is two or more fused aromatic rings wide and one or more fused aromatic rings in length. A method of exfoliating graphene nanoribbons in multi-layered graphene nanoribbon stack using the cyclophanes comprises the steps of exposing the multi-layered graphene nanoribbon stack to a solution comprising one or more of the cyclophanes, whereby the cyclophanes form polypseudorotaxanes with the graphene nanoribbons which results in the exfoliation of individual graphene nanoribbons as the result of Coulombic repulsion between the cyclophanes. Exposure of the multi-layered graphene nanoribbons to the cyclophanes can be accomplished by synthesizing the graphene nanoribbons in the presence of cyclophanes, such as, for example, ExBox•4X and Ex″Box•4X (n≥2). Alternatively, exposure can be accomplished by adding the cyclophanes to a solution of graphene nanoribbons after the nanoribbons have been synthesized. In each case, the resulting polypseudorotaxanes can be used to exfoliate the nanoribbons based on the Coulombic repulsion inherent between the tetracationic cyclophanes.

Methods for synthesizing the cyclophanes are described in detail in the examples. Briefly, the methods comprise the steps of reacting an extended bypyridine with α,α' dibromo-p-xylene to form a bromide salt of the extended bypyridine; converting the bromide salt into its hexafluorophate salt; and reacting the hexafluorophosphate salt with another molecule of the extended bipyridine to form the cyclophane. The step of reacting the hexafluorophosphate salt with the extended bipyridine may be done in the presence of a polyaromatic templating compound in order to improve yield. Like the PAHs that form inclusion complexes with the cyclophanes, the templating PAHs comprise two or more fused aromatic rings, which may be functionalized with alkyl groups, alkenyl groups, alkynyl groups and/or aryl groups.

EXAMPLES

Example 1

Synthesis of ExBox[4+] and its Use in Sequestering PAHs in Crude Oil

This example describes the synthesis and properties of a macrocyclic organic salt ExBox[4+], which serves as a high-affinity scavenger of an array of PAHs, up to the size of coronene, in both aqueous and organic media (FIG. 1). This example demonstrates the ability of ExBox[4+] to bind PAHs of different size and shape by means of donor—acceptor interactions on 11 examples of common PAHs ranging in size from two to seven aromatic rings, two of which (tetraphene and chrysene) are known for their mutagenicity/genotoxicity in somatic cells in experimental animals in vivo. The full solid-state characterization of the inclusion complexes of ExBox[4+] with all 11 PAHs is presented and its potential in the extraction and detection of harmful PAHs from the environment is discussed. Finally, the potential for the ExBox—PAH donor—acceptor superstructures to be used in organic field-effect transistors is considered.

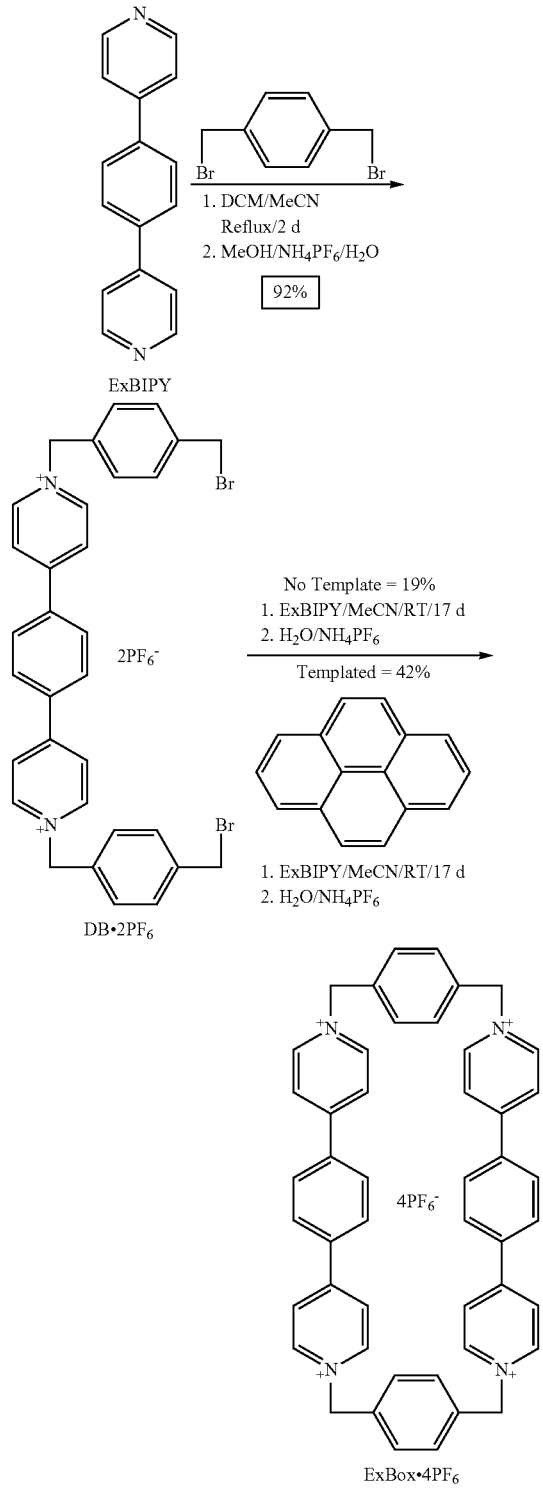

Scheme 1.

Reaction Scheme for the Synthesis of ExBox•4PF$_6$, Starting with the Reported Extended Bipyridine (ExBIPY)

Experimental

The full experimental details are provided after the examples. Below, the most important information is briefly summarized.

Single-Crystal X-ray Diffraction (XRD). Single crystals of ExBox•4PF$_6$ and its complexes 1-11 were grown by slow vapor diffusion of iPr$_2$O into solutions of ExBox•4PF$_6$ (or ExBox•4PF$_6$ and PAH guests (1:1.1)) in MeCN (3.0 mM) over the course of 1 week. Data were collected at 100 K on a Bruker Kappa APEX CCD diffractometer equipped with a Cu Kα microsource with Quazar optics.

Isothermal Titration Calorimetry (ITC). All ITC measurements were performed in dry, degassed MeCN at 298 K. A solution of ExBox•4PF$_6$ in MeCN was used as the host solution in a 1.8 mL cell. Solutions of aromatic guests in MeCN were added by injecting successively 10 μL of titrant over 20 s (25×) with a 300 s interval between each injection. Experiments were repeated three times. Thermodynamic information was calculated using a one-site binding model utilizing data from which the heat of dilution of the guest was subtracted, with the average of three runs reported.

Nuclear Magnetic Resonance (NMR) Spectroscopy. $^1$H NMR (298 K, 500 MHz) titrations were performed by adding small volumes of a concentrated guest solution/suspension in CDCl$_3$ to a solution of ExBox•4PF$_6$ in CD$_3$CN. Tetramethylsilane was used as a reference. Significant upfield shifts of the $^1$H resonances for γ protons were observed and used to determine the association constants ($K_a$). The $K_a$ values were calculated using Dynafit, a program that employs nonlinear least-squares regression on ligand—receptor binding data. In the case of 10 and 11, the low solubility of perylene and coronene prohibited the calculation of reliable $K_a$ values. The estimated $K_a$ value for 10 is reported, however, the error is substantial (76%).

Bisbromomethyl(bis-p-benzyl-4,4'-(1,4-phenylene)bispyridine)bis(hexyfluorophosphate) (DB•2PF$_6$). α,α'-Dibromop-xylene (4.58 g, 17.2 mmol) was added to CH$_2$Cl$_2$ (30 mL) in a 250 mL round-bottomed three-neck flask, and the resulting mixture was refluxed while stirring until all of the solid material dissolved. Next, the temperature of the oil bath was raised to 90° C., allowing the reaction mixture to reflux, while a suspension of ExBIPY (400 mg, 1.72 mmol) in MeCN (60 mL) was added in five aliquots slowly over 1 h. After only 30 min, however, a yellow precipitate, indicative of DB•2Br formation, began to appear. After heating under reflux for 48 h, the reaction mixture was cooled to room temperature, and the yellow precipitate was collected by filtration and washed with CH$_2$Cl$_2$. The yellow solid was dissolved in cold (≤25° C.) MeOH (~500-750 mL) followed by the addition of NH$_4$PF$_6$ (~100-200 mg) and cold (≤25° C.) H$_2$O (~2 L), resulting in the precipitation of pure DB•2PF$_6$ (1.41 g, 92%) that was collected by filtration as a white solid. HRMS-ESI for DB•2PF$_6$: calcd for C$_{32}$H$_{28}$Br$_2$F$_{12}$N$_2$P$_2$, m/z=743.0256 [M-PF$_6$]$^+$, 597.0536 [M-2PF$_6$]$^{2+}$; found, 743.0262 [M-PF$_6$]$^+$, 597.0538 [M-2PF$_6$]$^{2+}$. $^1$H NMR (500 MHz, CD$_3$CN, ppm): δ$_H$ 8.66 (AA' of AA'XX', J=6.9 Hz, 4H), 8.19 (XX' of AA'XX', J=6.9 Hz, 4H), 7.97 (s, 4H), 7.40 (AA' of AA'BB', J=8.2 Hz, 4H), 7.31 (BB' of AA'BB', J=8.2 Hz, 4H), 5.58 (s, 4H), 4.46 (s, 4H). $^{13}$C NMR (125 MHz, CD$_3$CN, ppm): δ$_C$ 155.0, 144.3, 139.9, 136.7, 132.9, 129.8, 129.1, 129.1, 125.6, 63.1, 32.3.

Cyclobis(4,4'-(1,4-phenylene)bispyridine-p-phenylene)-tetrakis(hexafluorophosphate) (ExBox•4PF$_6$). Two synthetic routes (Scheme 1), methods A (no template) and B (templated), were employed to prepare the tetracationic cyclophane. Method A: DB•2PF$_6$ (312 mg, 0.350 mmol) and ExBIPY (81.3 mg, 0.350 mmol) were added to dry MeCN (200 mL) and stirred at room temperature. After 17 days, the reaction was stopped by adding concentrated HCl (2-3 mL), which caused the crude product to precipitate from solution. The precipitate was collected by filtration, dissolved in H$_2$O, and precipitated again by adding NH$_4$PF$_6$ (~100-200 mg). The solid material was collected by filtration and then subjected to column chromatography using silica gel and 1% NH$_4$PF$_6$ in MeCN (w/v) as the eluent. The final product was purified further through recrystallization in MeCN on slow vapor diffusion of iPrO$_2$, yielding pure ExBox•4PF$_6$ (83 mg, 19%) as a white solid. Method B: DB•2PF$_6$ (312 mg, 0.350 mmol), ExBIPY (81.3 mg, 0.350 mmol), and the template pyrene (212 mg, 1.05 mmol) were added to dry MeCN (200 mL) and stirred at room temperature. After 17 days, the reaction was stopped by adding concentrated HCl (2-3 mL), causing the crude product to precipitate from solution. The yellowish-orange precipitate was collected by filtration and then dissolved in H$_2$O, followed by extracting 5× with CH$_2$Cl$_2$ (200 mL per extraction). This solvent extraction step changes the organic layer from an orange solution to a white suspension, indicating that most, if not all, of the template had been removed. The extracted material was precipitated from solution by adding NH$_4$PF$_6$ (~100-200 mg) before being subjected to column chromatography using silica gel and CH$_2$Cl$_2$/MeCN (1:1) and 1% NH$_4$PF$_6$ in MeCN (w/v) as the eluents, followed by recrystallization as in the case of nontemplated reaction to yield the pure product (184 mg, 42%) as a white solid. HRMS-ESI for ExBox•4PF$_6$: calcd for C$_{48}$H$_{40}$F$_{24}$N$_4$P$_4$, m/z=1107.2173 [M-PF$_6$]$^+$, 481.1263 [M-2PF$_6$]$^{2+}$; found, 1107.2184 [M-PF$_6$]$^+$, 481.1278 [M-2PF$_6$]$^+$. $^1$H NMR (500 MHz, CD$_3$CN, ppm): δ$_H$ 8.78 (AA' of AA'XX', J=7.0 Hz, 8H), 8.18 (XX' of AA'XX', J=6.9 Hz, 8H), 7.93 (s, 8H), 7.61 (s, 8H), 5.68 (s, 8H). $^{13}$C NMR (125 MHz, CD$_3$CN, ppm): δ$_C$ 155.5, 145.1, 137.4, 137.1, 131.1, 130.2, 126.7, 64.8. $^1$H NMR (500 MHz, CD$_3$COCD$_3$, ppm): δ$_H$ 9.28 (AA' of AA'XX', J=7.1 Hz, 8H), 8.51 (XX' of AA'XX', J=7.1 Hz, 8H), 8.15 (s, 8H), 7.86 (s, 8H), 6.08 (s, 8H). $^{13}$C NMR (125 MHz, CD$_3$COCD$_3$, ppm): δ$_C$ 155.2, 145.5, 137.4, 137.3, 131.3, 130.2, 126.6, 64.7.

The chemical constitution of ExBox•4X and Ex″Box•4X (n≥2) is based on the family of π-electron-poor viologen salts, more specifically the phenylene-bridged 4,4'-bipyridiniums which are known as "extended viologens." The typical synthesis—which generates the hexafluorophosphate salt of ExBox•4X—begins by treating the extended bipyridine (ExBIPY) with an excess of α,α'-dibromo-p-xylene in a refluxing MeCN/CH$_2$Cl$_2$ solvent mixture (2:1), which initially produces the yellow, bromide salt (DB•2Br) after two days. In order to render the initial viologen salt soluble in organic media for the next step, the bromide salt is converted to the hexafluorophosphate salt (DB•2PF$_6$) by first dissolving DB•2Br in MeOH—as opposed to H$_2$O as a consequence of the poor solubility of DB•2Br and potential hydrolysis at the benzylic positions—followed by the addition of solid NH$_4$PF$_6$ and subsequent precipitation of DB•2PF$_6$ after copious amounts of H$_2$O is added (approximately a few liters for every 500 mL of MeOH used). In the final step, two synthetic pathways lead to the final viologen-based tetracationic cyclophane (ExBox•4PF$_6$). The first pathway consists of simply mixing DB•2PF$_6$ and ExBIPY in a 1:1 ratio in MeCN and allowing the reaction to proceed for a little over two weeks. The yield from this reaction, however, is low (19%). Therefore, a method involving templation was adopted wherein six equivalents of pyrene are used to help stabilize the transition state during cyclophane closure as a result of donoracceptor interactions between the π-electron-rich pyrene and the π-electron-poor extended viologen units of ExBox$^{4+}$. Moreover, the pyrene template is removed easily by solvent extraction with CH$_2$Cl$_2$—which changes the organic layer from an orange solution to a white suspension—after the desired cyclophane has been converted to the chloride salt (ExBox•4Cl, not shown). The final step of the synthesis involves another counterion exchange wherein the chloride salt (ExBox•4Cl) is converted to the hexafluorophosphate salt by adding solid $NH_4PF_6$, an action which precipitates white ExBox•4$PF_6$ from the water layer. This method affords the desired product in 42% yield after silica column chromatography—1% $NH_4PF_6$ in MeCN (w/v) and several recrystallizations.

From a photophysical perspective, ExBox$^{4+}$ demonstrates a strong absorbance in the ultraviolet region at 319 nm. Upon addition of a π-electron-rich guest and formation of a 1:1 complex (ExBox$^{4+}$ ⊂ guest), the optical absorption data show the emergence of a charge-transfer band (400-650 nm) in the visible region of the spectrum. All of the electron-donating guests assessed (FIG. 1), with the exception of azulene and tetracene, exhibit this behavior. In the case of the former, there appears to be no change in the absorption spectra when ExBox$^{4+}$ is mixed with azulene in a 1:1 ratio, as compared to the superposition of the individual molecular spectra. No absorption data were obtained for the ExBox$^{4+}$ ⊂ tetracene inclusion complex because of solubility issues associated with tetracene. It is important to note that the ExBox ⊂ tetracene•4$PF_6$ single crystals (5), shown in FIG. 1, were obtained by first heating the 1:1 mixture of the π-electron-rich guest and ExBox$^{4+}$ in PhMe/MeCN (1:1) prior to dilution with an additional MeCN and crystallization.

Analysis of the cyclic voltammogram (CV) of ExBox$^{4+}$ and the phenylene-bridged methyl viologen (MPV$^{2+}$) provides some insight into the electrochemical behavior of the extended viologen units on an individual basis as well as when more than one unit is part of a rigid cyclophane. The CV of MPV$^{2+}$ comprises one broad redox couple where the two one-electron reduction waves overlap completely at –0.82 V, an observation which is an indication that the two bipyridinium redox centers are not communicating and behave quite independently of one another. Conversely, the CV of ExBox$^{4+}$ comprises two closely overlapping two-electron redox couples, where the potentials of the two cathodic peaks are separated by 140 mV. This separation reflects the level of electronic communication between the two redox centers of each extended bipyridinium unit insofar as that, after formation of the radical cationic ExBox$^{2(•+)}$, the second two-electron reduction, which leads to the formation of the neutral species, is shifted to lower potentials and is therefore more difficult to reduce. This direct comparison demonstrates how the electronic properties of the extended viologen units can be altered by controlling the steric and electronic environment as well as incorporating them into a rigid cyclophane.

FIG. 1 illustrates the superstructures of hostguest complexes of ExBox$^{4+}$ with 11 PAH guests viewed from different angles, as obtained from the XRD analysis of single crystals of these complexes. They demonstrate the remarkable ability of ExBox$^{4+}$ to scavenge a large number of PAHs varying in size (from azulene up to coronene) and shape (from linear tetracene to star-like triphenylene).

High-quality single crystals of ExBox$^{4+}$ and its inclusion complexes were obtained by slow vapor diffusion of $iPr_2O$ into the solution of ExBox$^{4+}$ and the 1:1.1 stoichiometric mixtures of ExBox$^{4+}$ with the PAHs in MeCN over a period of a few days. The color of these crystals corresponds to the absorption wavelength of the charge-transfer band of the corresponding complex in solution and makes it possible for one to detect visually when a PAH molecule binds inside ExBox$^{4+}$. This feature makes ExBox$^{4+}$ a suitable candidate for visual PAH sensing.

The dimensions of the cavity of ExBox$^{4+}$ are 6.9 Å (width)×14.6 Å (length) as deduced from the distances between the aromatic planes on opposite sides of the empty cyclophane in the X-ray crystal structure and approximately 3.5 Å (width)×11.2 Å (length) when considering the van der Waals radii. ExBox$^{4+}$ binds π-electron-rich guests effectively as a result of its inherent π-π stacking distances (3.5 Å) between the π-electron-poor units of the host and the guest. The ability of ExBox$^{4+}$ to bind large PAH guests is a consequence of the inside length parameter of ExBox$^{4+}$ (approximately 7.8 Å). Coronene is the largest guest (in one dimension) investigated in this example. In principle, thin graphene nanoribbons that would be "coronenewide" in one dimension (i.e., approximately 7.3 Å) could potentially serve as a guest for multiple host molecules of ExBox$^{4+}$.

The general trend, which becomes evident when comparing the crystal superstructures of 1-11, is that each PAH guest adopts the greatest possible π-π overlap with the extended bipyridinium (ExBIPY$^{2+}$) units of ExBox$^{4+}$. This principle can be demonstrated quite nicely by comparing the two linear PAH molecules, anthracene and tetracene. While the shorter anthracene (7.3 Å) is fully aligned inside ExBox$^{4+}$, the length of tetracene (9.7 Å) overcomes the size limit of ExBox$^{4+}$ and is forced out of colinearity by approximately 44°, and the two terminal benzenoid rings protrude outside the cavity (FIG. 1). Also, as the size of the PAH guest is increased, the torsion angles between the pyridinium and the phenylene rings of ExBox$^{4+}$ tend to decrease, reaching a lower limit in the case of perylene.

The size and shape of the PAH guests play an important role also on the overall packing (FIG. 4) in the crystal. Generally, the smaller PAHs (1-4) crystallize in a 2:1 (PAH:ExBox$^{4+}$) manner, where one PAH molecule binds inside ExBox$^{4+}$ and the second molecule is located in the outer space interacting through C—H . . . π interactions with ExBox$^{4+}$ or the complexed PAH molecules, while the larger PAHs (7-11) crystallize in a 1:1 (PAH:ExBox$^{4+}$) fashion, where all of the PAH molecules are inside ExBox$^{4+}$. The two exceptions (5 and 6) to this experimental observation, which are, sizewise, somewhere in between the smaller and larger studied PAHs, crystallize in a 1:2 (PAH:ExBox$^{4+}$) manner; half of the ExBox$^{4+}$ hosts in the superstructure being empty. This phenomenon could play an important role in the tuning of the overall properties of such "superstacks" when considering their possible functions as organic semiconductors. Additionally, a certain degree of disorder of PAH molecules, either inside or outside of ExBox$^{4+}$ or both, in the superstructure was observed in some cases (1, 3, 5, 6, 8, and 9).

The least planar guest [4]helicene possesses a twisted helical conformation, demonstrating the ability of ExBox$^{4+}$ to bind PAHs is not strictly limited to the planar guests. The high-affinity diverse binding capability of ExBox$^{4+}$ arises, presumably, from the locally flexible character of this globally rigid cyclophane.

The thermodynamic parameters (ΔH, ΔS, and ΔG) and the association constants ($K_a$) for the 1:1 complexes of ExBox$^{4+}$ with PAH guests (1-11) in solution (MeCN) are summarized in FIG. 7. The thermodynamic parameters for the binding events of ExBox$^{4+}$ with the PAHs (complexes 3, 4, 6, and 8) were obtained by ITC in dry, degassed MeCN at 298 K. The restricted solubility of the remainder (complexes 1, 2, 5, 7, and 9-11) of the PAHs in MeCN prohibited the use of ITC to monitor the thermodynamic parameters of binding. $^1$H NMR spectroscopy was used to obtain $K_a$ values for the association between ExBox$^{4+}$ and the PAHs which are, at least partially, soluble in CDCl$_3$ (complexes 1, 2, 7, 9, and 10). In the case of complexes 5 and 11, the extremely low solubility of tetracene and coronene, respectively, in most organic solvents rendered it impractical to obtain $K_a$ values for these complexes.

Comparison of the full thermodynamic parameters available for the four complexes 3, 4, 6, and 8 leads to the conclusion that the host guest binding process is mainly enthalpy driven in the case of 3, 6, and 8. With 4, however, a surprisingly small change in entropy ($\Delta S$), which contributes to the large $K_a$ value for this complex, was observed. Although the complexes of ExBox$^{4+}$ with 4 and 6 have very similar values of $\Delta H$, the $K_a$ values for the complex with 6 differs by approximately a factor of 7 compared with that for 4. This low value of $\Delta S$ in the case of 4 could be caused by the presence of dimeric forms of pyrene in MeCN, decreasing the entropy of the initial (prior-to-complexation) state.

The $^1$H NMR spectra (FIG. 2A-2F) of the 1:1 ExBox$^{4+}$ ⊂PAH complexes display significant upfield shifts for the signals corresponding to β and γ protons of ExBox$^{4+}$ and all of the signals for the protons of the PAH guests as well as a downfield shift of the phenylene protons of ExBox$^{4+}$. This pattern is caused by π-electron shielding of the face-to-face oriented aromatic rings, which occurs upon complexation. The α and CH$_2$ protons of ExBox$^{4+}$ display only very slight shifts in their $^1$H NMR spectra since they are located in the "corners" of ExBox$^{4+}$ and are therefore not affected significantly by the shielding effect of PAH guests. This behavior is in excellent agreement with the inclusion of PAH guests inside ExBox$^{4+}$ in the solution state. Additionally, it is important to note that there are only one set of proton signals observed for ExBox$^{4+}$ and the guest, as a result of the various species that exist in equilibrium undergoing fast exchange on the $^1$H NMR time scale.

Figure 3A:
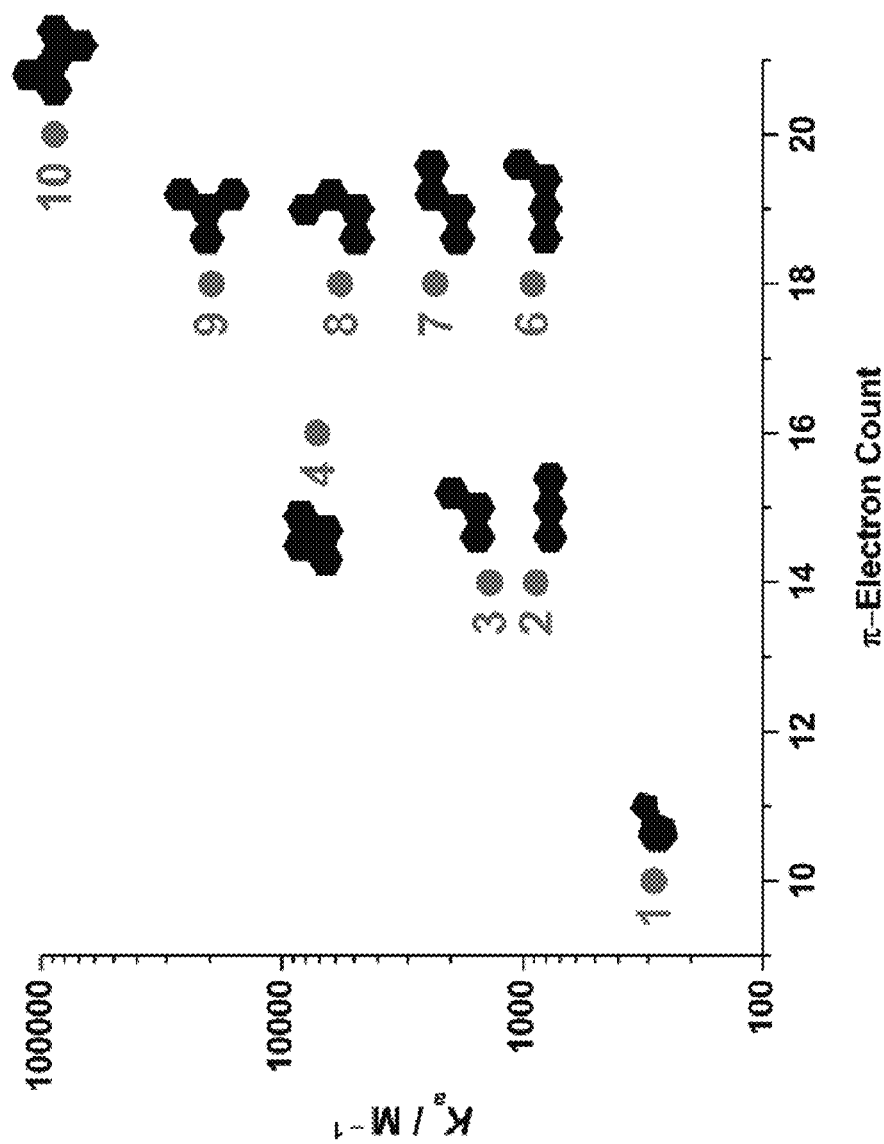
FIG. 3. The $K_a$ values (A) and the chemical shift differences of the γ protons of ExBox$^{4+}$ (7.93 ppm) and its 1:1 complex (Δδ of H$_γ$) (B) plotted against the number of π-electrons present in the respective PAH. Both $K_a$ values (exponential behavior; logarithmic scale was used for the y-axis) and Δδ values for H$_γ$ (linear behavior) increase as the number of π-electrons became larger and larger and show that the binding affinity of ExBox$^{4+}$ towards PAHs is related directly to the increase of the size of the PAH core.
Figure 3B:
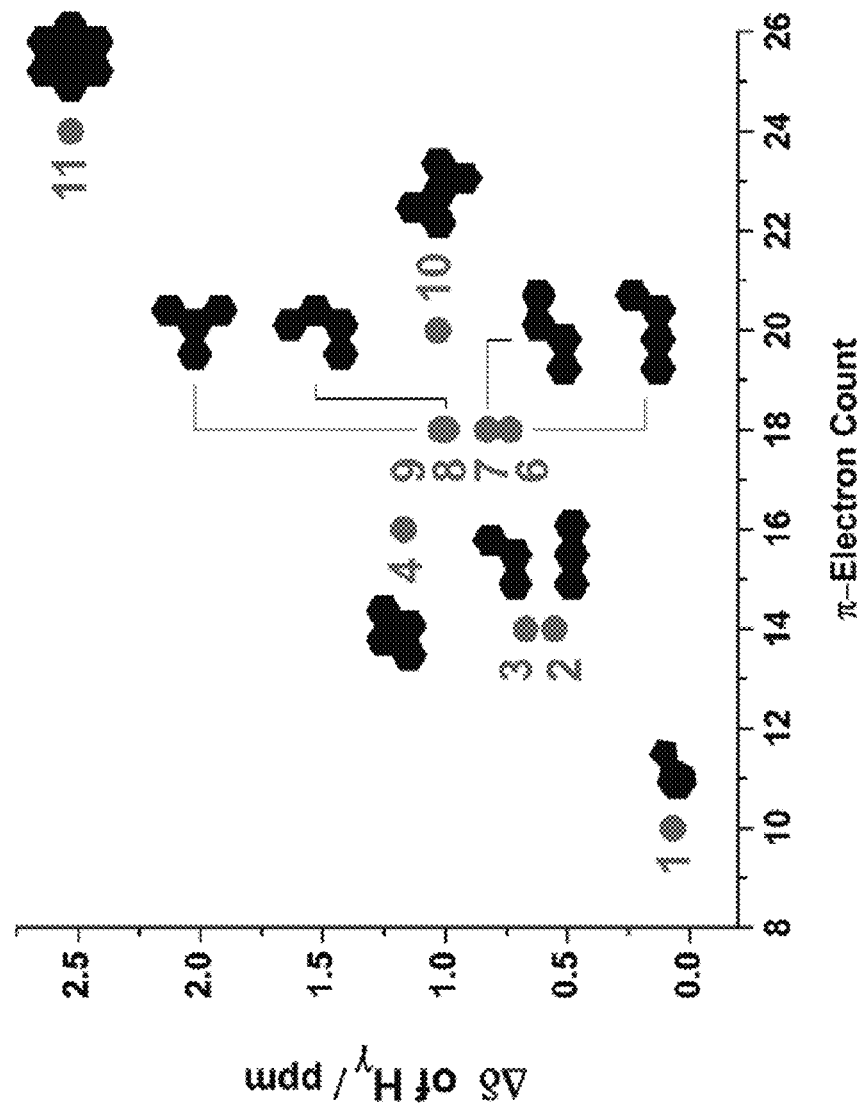
Figure 4A:
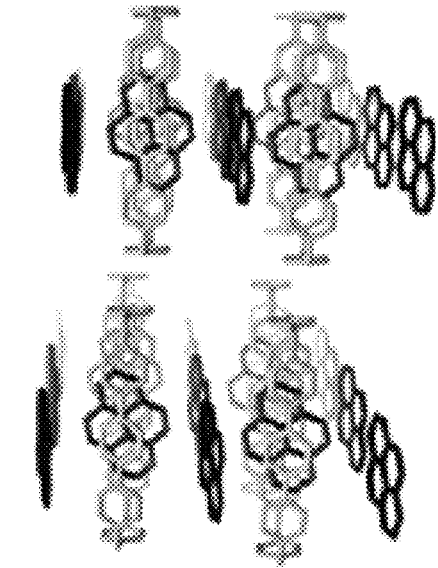
FIG. 4. Superstructures of the four inclusion complexes ExBox ⊂ anthracene•4PF$_6$(anthracene) (A), ExBox ⊂ pyrene•4PF$_6$(Pyrene) (B), ExBox ⊂ perylene•4PF$_6$ (C), and ExBox ⊂ coronene•4PF$_6$ (D). The superstructures were generated from X-ray crystallography carried out on single crystals that were grown at a higher concentration (3.0 mM) and used to obtain the single-crystal XRD data shown in FIG. 1. In the case of the superstructures where a smaller guest was employed, i.e., three and four rings, it should be noted that the sheets of inclusion complexes are separated by sheets of the free guest (A,B), whereas in the case of the larger guests, the packing in the crystal consists of only the 1:1 inclusion complexes and no intercalated PAHs are observed (C,D). The PF$_6^-$ counterions and the solvent molecules in the superstructures are omitted for clarity.
Figure 4B:
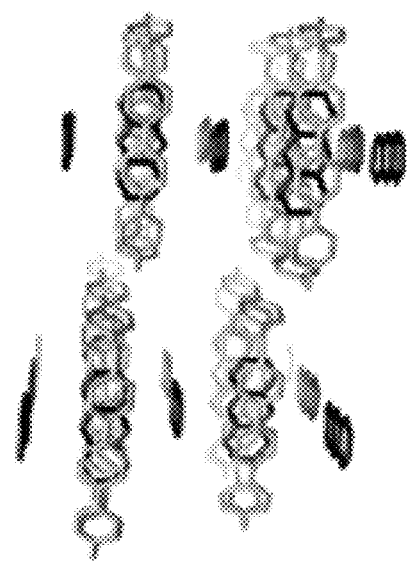
Figure 4C:
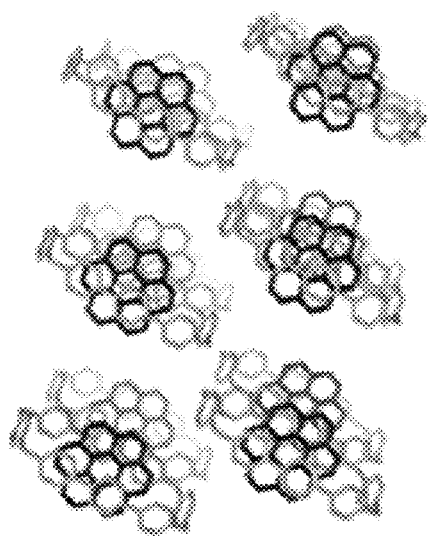
Figure 4D:
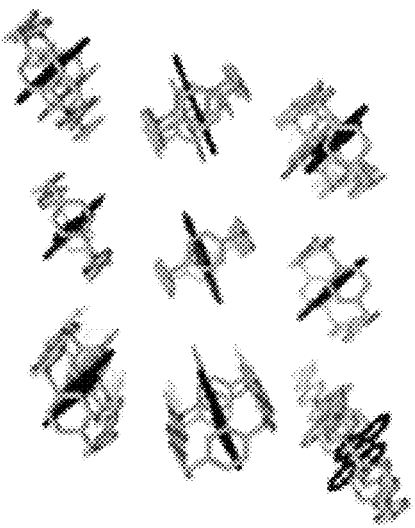

A general trend associated with the binding affinity of ExBox$^{4+}$ toward PAH guests exists, whereby the stability constant of the complex increases exponentially (FIG. 3A) as the PAH guests become more π-electron-rich resulting in greater π-π (interactions between the host and guest. This trend is exhibited by all of the complexes, except for 6-8 which cannot adopt maximum π-π overlap on account of the unfavorable size/shape of the PAH guest. The side-on view (FIG. 1) of the crystal superstructure of 6-9 reveals that the face-to-face π-π overlaps between ExBox$^{4+}$ and the PAH molecules increase with higher and higher $K_a$ values. A similar (although linear) trend is observed (FIG. 3B) when the difference between the chemical shifts (in ppm) of the γ protons of the 1:1 complexes and those for the unbound ExBox$^{4+}$ is plotted against the number of π-electrons in the PAH molecule. In this case, the chemical shift not only depends on the $K_a$ value, which correlates to the number of π-electrons, but also directly on the number of π-electrons as they dictate the shielding effect of the PAH guest.

Four PAH guests (varying between three and seven rings) were explored in a solid-state setting on SiO$_2$ platforms in the form of 2:1 or 1:1 inclusion complexes with ExBox$^{4+}$. By lowering the concentration of the host and guest to 0.625 and 0.750 mM in MeCN, respectively, micrometer-sized single crystals were obtained for ExBox⊂anthracene 4PF$_6$(anthracene) (three rings, FIG. 4A), ExBox⊂pyrene 4PF$_6$ (pyrene) (four rings, FIG. 4B), ExBox⊂perylene•4PF$_6$ (five rings, FIG. 4C), and ExBox⊂coronene•4PF$_6$ (seven rings, FIG. 4D). Their scanning electron microscopy (SEM) images, provide a sense of the crystal morphology of each of the complexes that were grown on the SiO$_2$ surface. The superstructures of each complex, shown in FIG. 4, demonstrate the packing of the individual inclusion complexes. In the case of anthracene (FIG. 4A) and pyrene (FIG. 4B), the molecules are ordered in an alternating fashion, whereby the inclusion complexes are intercalated with continuous sheets of the electron-rich PAHs, a feature which could lead potentially to these materials functioning in an organic field-effect transistor. In the perylene (FIG. 4C) and coronene (FIG. 4D) superstructures, however, the individual complexes do not appear to pack into discrete donoracceptor domains but instead are organized through intermolecular steric interactions between each complex.

Figure 5A:
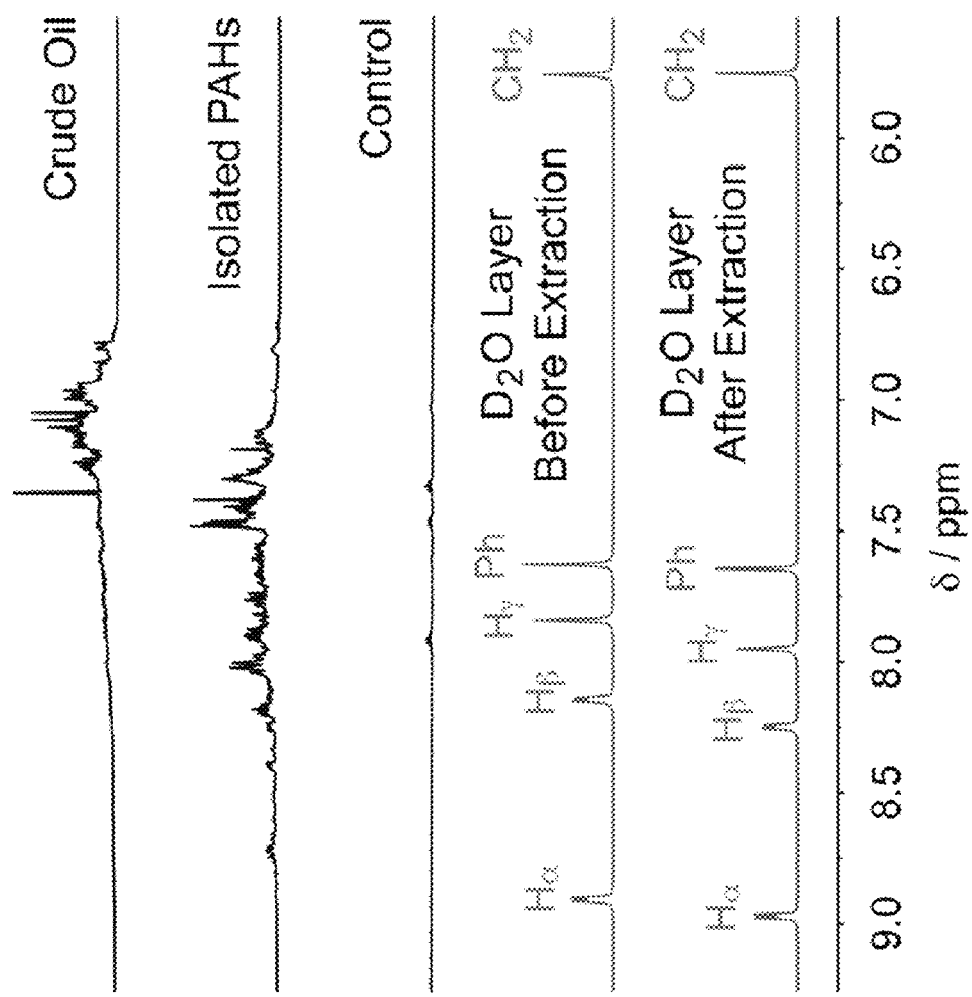
FIG. 5A. $^1$H NMR spectra for the crude oil sample from Saudi Arabia, as described in Example 1.
Figure 5B:
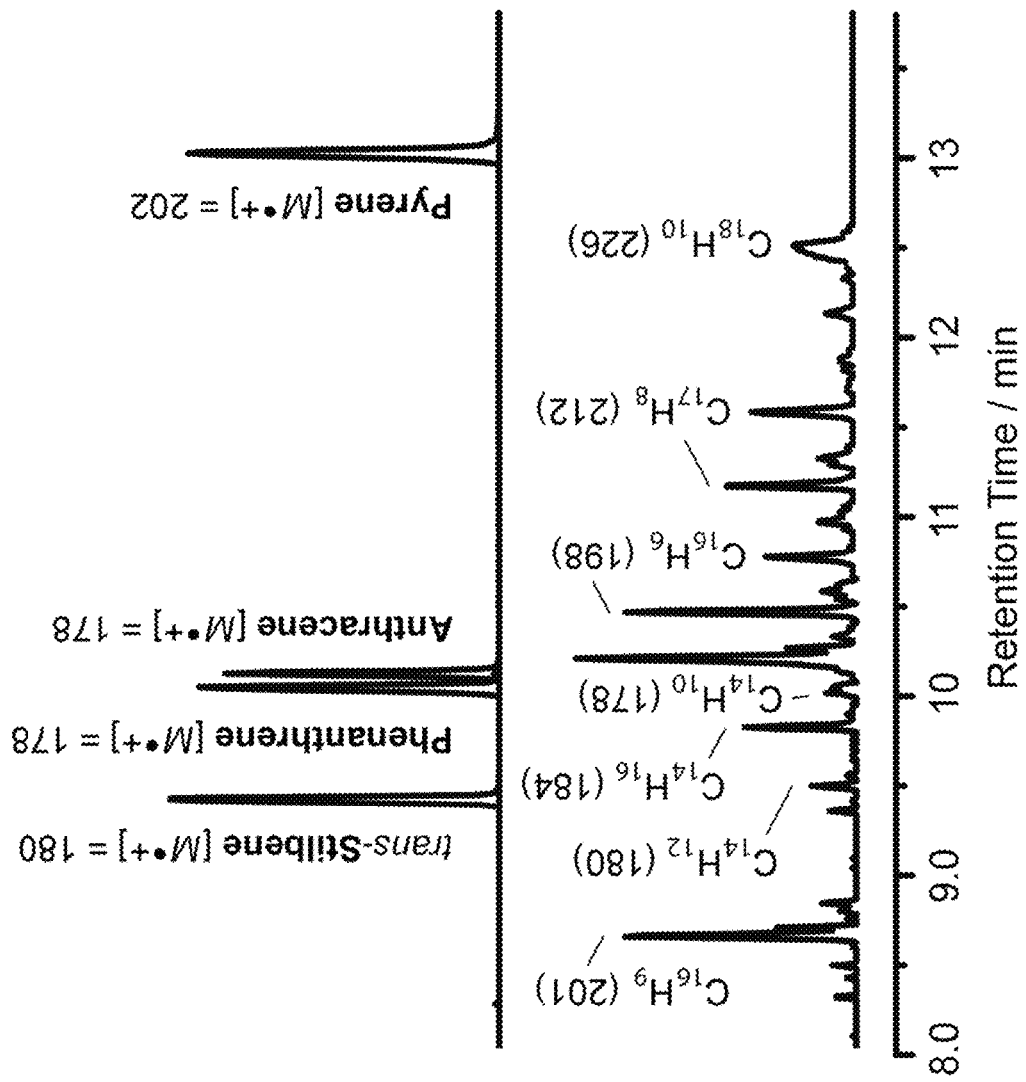
FIG. 5B. GC-MS data for four PAH standards (top) and compared to the material that was extracted from the crude oil. From this MS data, it is possible to generate molecular formulas, which correspond to various PAH derivatives that fall within the mass range of the tested standards.
Figure 6A:
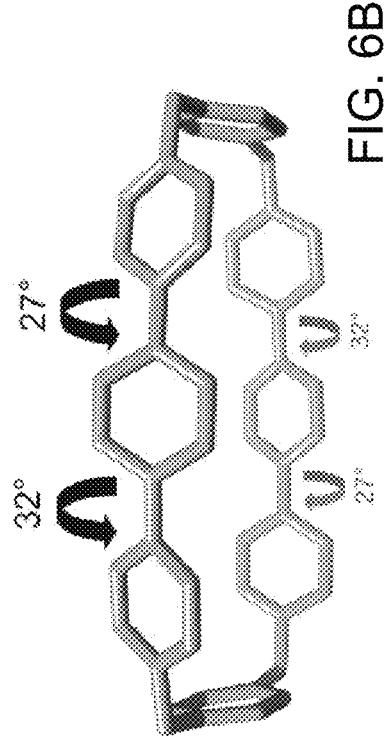
Figure 6B:
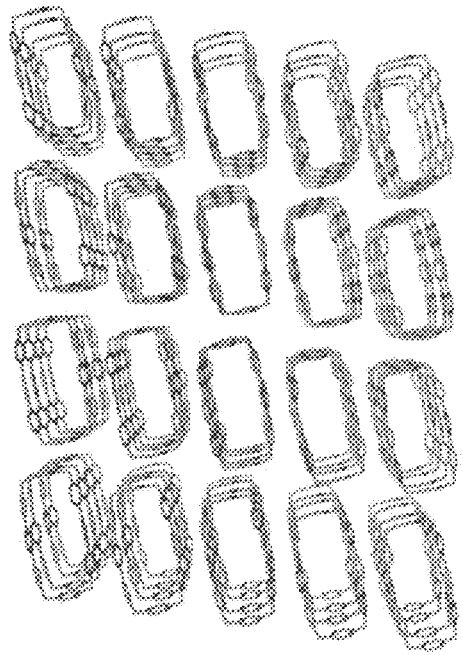
FIG. 6(B) side view of ExBox•4PF$_6$.
Figure 6C:
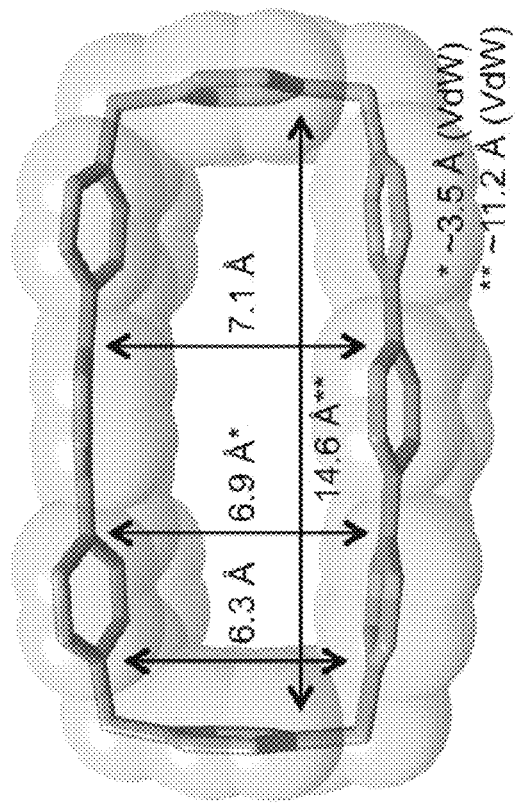
FIG. 6(C) a-axis view of ExBox•4PF$_6$.
Figure 6D:
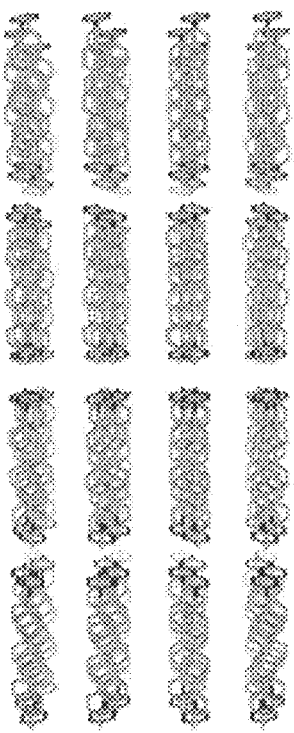
FIG. 6(D) b-axis view of ExBox•4PF$_6$.

In order to demonstrate the high affinity that ExBox$^{4+}$ has for PAHs in a mixture of hydrocarbons, a crude oil sample from Saudi Arabia containing an unspecified array of aromatic compounds was tested against ExBox•4Cl in water. The results of this investigation are summarized in FIG. 5. The starting crude oil mixture was first diluted (i) with CD$_2$Cl$_2$ (150 μL of oil added to 4 mL) before the addition (ii) of ExBox•4Cl in 4 mL of D$_2$O (8 mM) on top of the oil, taking care not to disturb the oily layer. The vial is the control mixture where 4 mL of D$_2$O only was added to the oily layer, and it was later found to contain no PAHs. After shaking the oil-water mixture (which contains ExBox$^{4+}$) by hand for approximately 2 min (iii), the color of the aqueous phase turned to an orange-yellow hue, which is different from the previous lighter-colored suspension before the two phases had been mixed. After separation of the two phases, the aqueous layer was siphoned off and the newly acquired aromatic guests were isolated (iv) by solvent extraction using a few iterations of CH$_2$Cl$_2$, while simultaneously regenerating the ExBox$^{4+}$ in aqueous solution. $^1$H NMR spectra recorded at each stage of the PAHs isolation procedure are presented in FIG. 5A. The spectrum at the top of FIG. 5B shows $^1$H NMR peaks in the aromatic region present in the starting oily layer. The $^1$H NMR spectrum directly below the crude oil spectrum shows that ExBox$^{4+}$ has been successful in extracting a range of different aromatic hydrocarbons in the crude oil. The $^1$H NMR spectrum of ExBox$^{4+}$ before the two phases were mixed shows the starting chemical shifts of each proton in the aromatic region in D$_2$O, whereas the spectrum recorded after extraction of aromatics from the crude oil solution shows small changes in the chemical shifts of the α, β, and phenylene protons and a more dramatic shifting of the resonances for the γ protons. In an effort to characterize the extracted aromatic compounds, GC-MS studies were conducted on four standards (trans-stilbene, phenanthrene, anthracene, and pyrene; FIG. 5B) as well as the mixture of aromatic compounds that were extracted from the crude oil in steps iii and iv. This general MS characterization makes it possible to generate mass ranges and molecular formulas for the extracted aromatic material and gives a sense of the sizes of compounds ExBox$^{4+}$ is capable of scavenging. Overall, the oil extraction study demonstrates clearly the ability of ExBox$^{4+}$ to pull out potentially harmful PAHs from a crude mixture of oil, which contains a large number of different aromatic hydrocarbons.

Example 2

Synthesis of Ex″Box$^{4+}$

The synthesis of Ex″Box•4X (n≥2) is carried out in the fashion as described in Example 1. The Ex$^2$Box•4X was prepared in this way in 10% yield using pyrene as a template. The reaction scheme for the synthesis of Ex″Box•4X (n≥2) is shown in Scheme 2:

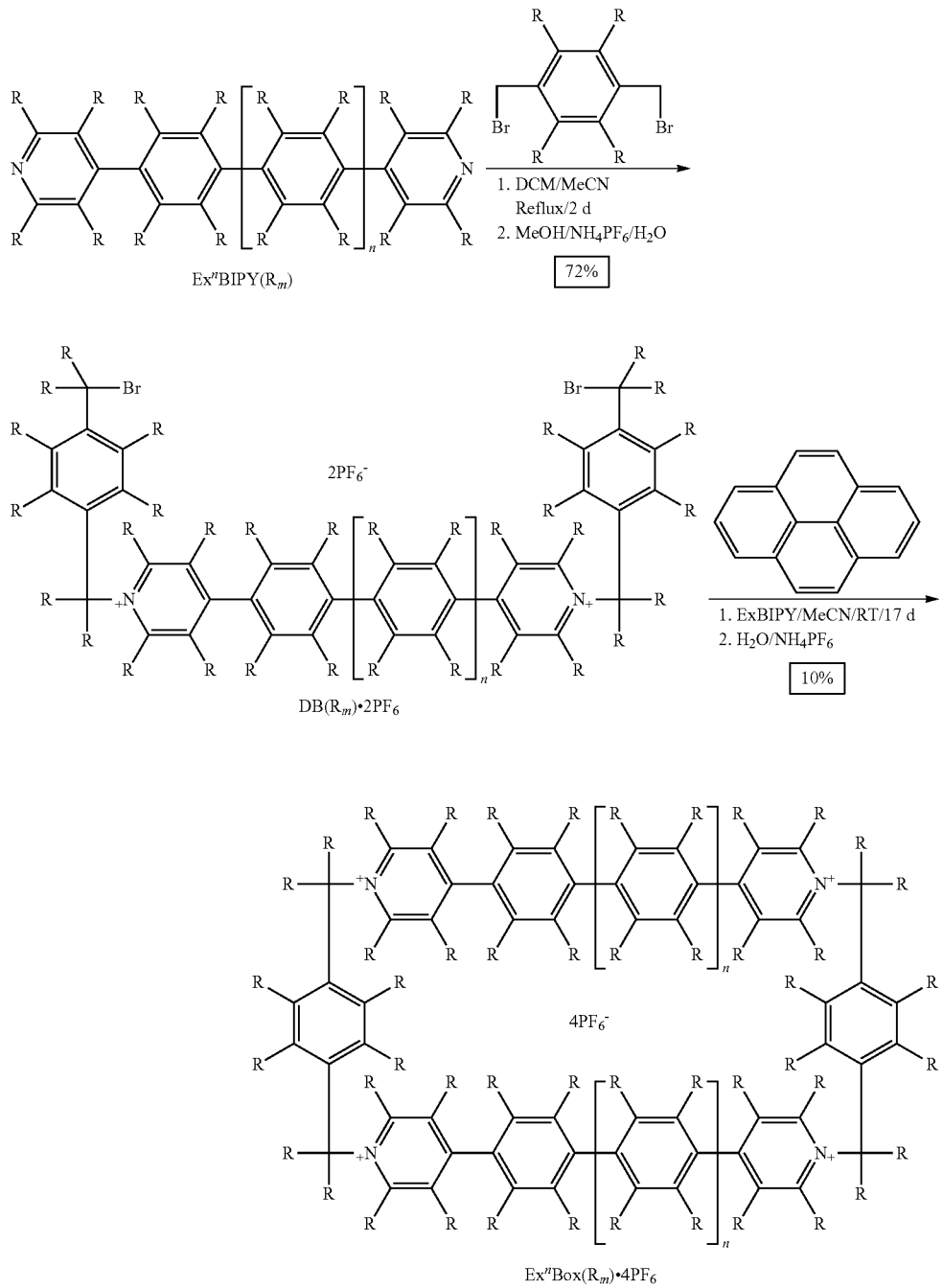

Cyclobis(4,4'-(1,4-biphenylene)bispyridin-1-ium-1,4-phenylenebis(methylene))tetrakis-(hexafluorophosphate) (Ex²Box•4PF$_6$). A solution of DB•2PF$_6$ (600 mg, 0.621 mmol), Ex²BIPY (192 mg, 0.621 mmol), and the template pyrene (754 mg, 3.73 mmol) in dry MeCN (450 mL) was stirred at room temperature for 17 d (Scheme 3). The reaction was stopped by adding concentrated HCl (2-3 mL), causing the crude product to precipitate from solution. The yellowish precipitate was collected by filtration and dissolved in hot MeOH. The crude Ex²Box•4PF$_6$ was precipitated from solution by adding NH$_4$PF$_6$ (~0.5 g) and an excess of H$_2$O before being subjected to column chromatography using silica gel and CH$_2$Cl$_2$/MeCN (1:1) and 0.25-0.5% NH$_4$PF$_6$ in MeCN (w/v) as the eluents, followed by recrystallization in MeCN on slow vapor diffusion of iPr$_2$O, yielding pure Ex²Box•4PF$_6$ (87 mg, 10%) as a pale yellow solid. HRMS-ESI for Ex²Box•4PF$_6$: calcd for C$_{60}$H$_{48}$F$_{24}$N$_4$P$_4$: m/z=1259.2799 [M-PF$_6$]$^+$, 557.1576 [M-2PF$_6$]$^{2+}$. found: 1259.2792 [M-PF$_6$]$^+$, 557.1590 [M-2PF$_6$]$^{2+}$. $^1$H NMR (500 MHz, CD$_3$CN, ppm): $\delta_H$ 8.74 (AA' of AA'XX', J=7.0 Hz, 8H), 8.18 (XX' of AA'XX', J=6.9 Hz, 8H), 7.89 (AA' of AA'BB', J=8.6 Hz, 8H), 7.84 (BB' of AA'BB', J=8.6 Hz, 8H), 7.63 (s, 8H), 5.67 (s, 8H). $^{13}$C NMR (125 MHz, CD$_3$CN, ppm): $\delta_C$ 156.4, 144.8, 143.4, 137.0, 133.9, 131.0, 129.6, 129.1, 126.0, 64.5. The reaction scheme for the synthesis of Ex²Box•4PF$_6$ is shown in Scheme 3:

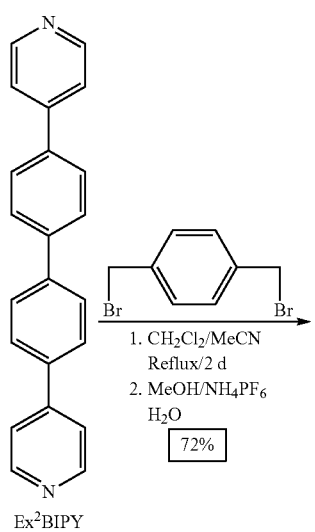

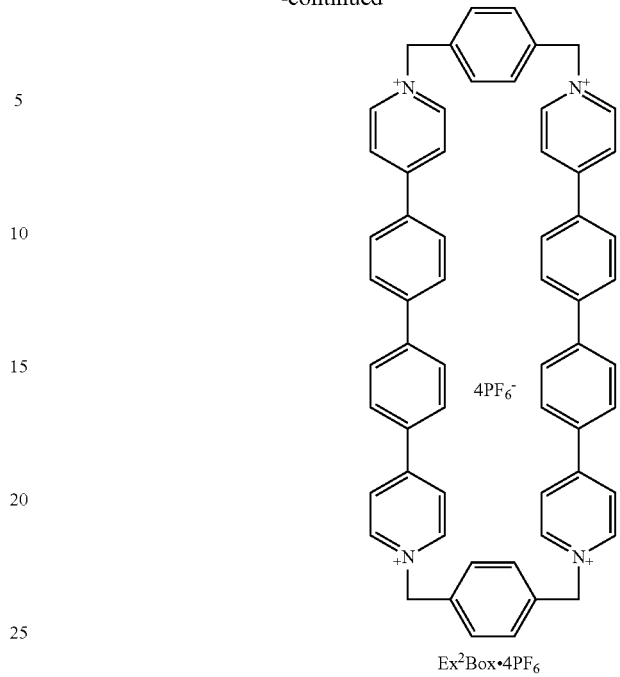

Example 3

Synthesis of Functionalized Ex″Box(Rm)•4X Cyclophanes

The incorporation of R substituents into ExBox•4X and Ex″Box•4X (n≥2) is done by introducing the R groups onto Ex″BIPY, which is then carried through to the synthesis of DB(R$_m$)•2X.

Full Experimental Details for the Examples:

Section A. Materials/General Methods/Instrumentation

All reagents were purchased from commercial suppliers (Aldrich or Fisher) and used without further purification. The crude oil samples were purchased from ONTA Inc., (Geology) Coal and Petroleum/Crude Oil Samples based out of Ontario, Calif. (www.onta.com) and were diluted with CD$_2$Cl$_2$ before extraction. Analytical high-performance liquid chromatography (HPLC) was performed on reverse phase-HPLC (RP-HPLC) instruments, using a C$_{18}$ column and a binary solvent system (MeCN and H$_2$O with 0.1% CF$_3$CO$_2$H). Thin-layer chromatography (TLC) was performed on silica gel 60 F254 TLC plates (Merck). Column chromatography was carried out on silica gel 60F (Merck 9385; 0.040-0.063 mm). UV/Vis Absorbance spectra were recorded using a UV-3600 Shimadzu spectrophotometer. Nuclear magnetic resonance (NMR) spectra were recorded on a BrukerAvance 600 and Varian P-Inova 500 spectrometers, with working frequencies of 600 and 500 MHz, respectively. Chemical shifts are reported in ppm relative to the signals corresponding to the residual non-deuterated solvents (CD$_3$CN: $\delta_H$=1.94 ppm and $\delta_C$=1.32 ppm; CDCl$_3$: $\delta_H$=7.26 ppm; CD$_2$Cl$_2$: $\delta_H$=5.32 ppm; CD$_3$COCD$_3$: $\delta_H$=2.05 ppm and $\delta_C$=29.84 ppm; D$_2$O: $\delta_H$=4.79 ppm). High-resolution mass spectra (HRMS) were measured on an Agilent 6210 Time of Flight (TOF) LC-MS, using an ESI source, coupled with Agilent 1100 HPLC stack, using direct infusion (0.6 mL min$^{-1}$). Isothermal titration calorimetry (ITC) experiments were performed on a MicroCal system, VP-ITC model.

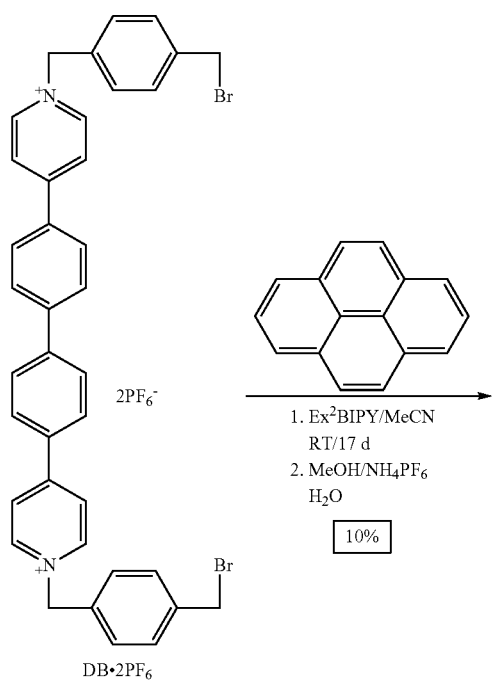

Cyclic voltammetry (CV) experiments were carried out at room temperature in argon-purged solutions of DMF with a Gamry Multipurpose instrument (Reference 600) interfaced to a PC. All CV experiments were performed using a glassy carbon working electrode (0.071 cm$^2$). The electrode surface was polished routinely with 0.05 μm alumina—water slurry on a felt surface immediately before use. The counter electrode was a Pt coil and the reference electrode was a Ag/AgCl electrode. The concentration of the sample and supporting electrolyte, tetrabutylammonium hexafluorophosphate (TBAPF$_6$), were 1.0 mM and 0.1 M, respectively. The CV cell was dried in an oven immediately before use, and Ar was continually flushed through the cell as it was cooled down to room temperature to avoid condensation of water. SEM imaging was performed on a FEI Quanta 600F sFEG ESEM scanning electron microscope (SEM) at an accelerating electron voltage of 30 kV under high vacuum.

4,4'-(1,4-Phenylene)bispyridine—"Extended Bipyridine=ExBIPY"

ExBIPY: Pyridylboronic pinacol ester (3.64 g, 17.8 mmol), 1,4-dibromobenzene (1.40 g, 5.92 mmol), and Cs$_2$CO$_3$ (11.6 g, 35.5 mmol) were added to a 1:1 mixture of dry PhMe/DMF (300 mL), which had been degassed with Ar for 15 min. Next, Pd(PPh$_3$)$_4$ (0.68 g, 0.59 mmol) was added to the reaction mixture and the solution heated to 130° C. under Ar for 48 h. Then, the reaction mixture was cooled to room temperature and the palladium catalyst filtered off using Celite. The organic phase was concentrated under vacuum and then dissolved in CH$_2$Cl$_2$ followed by extraction with H$_2$O three times. The organic layer was made acidic (pH 2-3) by adding dropwise concentrated HCl, which caused the desired product to precipitate from solution. The precipitate was collected by filtration and then dissolved in H$_2$O. Finally, aq. NaOH (10 M) was added dropwise to the water layer until the pH was ~8-9, which resulted in precipitation of pure product ExBIPY (973 mg, 71%) as a white solid. The yield of the product obtained in the reaction was 71%. $^1$H NMR (500 MHz, CDCl$_3$, ppm): δ$_H$ 8.72 (AA' of AA'XX', J=4.6, 1.6 Hz, 4H), 7.80 (s, 4H), 7.59 (XX' of AA'XX', J=4.6, 1.6 Hz, 4H).

Cyclobis(4,4'-(1,4-phenylene)bispyridine-p-phenylene) tetrachloride—"Extended Viologen Box=ExBox•4Cl"

ExBox•4Cl: For the purposes of PAHs extraction from crude oil, ExBox•4PF$_6$ (50 mg, 0.040 mmol) was converted to the water-soluble chloride salt by dissolving it in MeCN (50 mL) and adding tetrabutylammonium chloride (~50 mg) to precipitate ExBox•4Cl from solution. The precipitate was collected by filtration, washed with MeCN (100-200 mL), and dried in vacuum to afford pure ExBox•4Cl (32 mg, 98%) as a white solid. $^1$H NMR (500 MHz, D$_2$O, ppm): δ$_H$ 8.91 (AA' of AA'XX', J=6.4 Hz, 8H), 8.15 (XX' of AA'XX', J=6.3 Hz, 8H), 7.84 (s, 8H), 7.63 (s, 8H), 5.76 (s, 8H). $^{13}$C NMR (125 MHz, D$_2$O, ppm): δ$_C$ 155.1, 143.7, 136.5, 136.0, 129.9, 128.8, 125.7, 63.8.

[4]Helicene

Scheme 4.

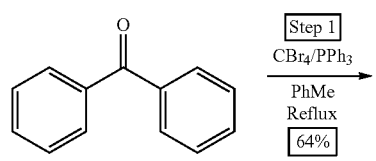

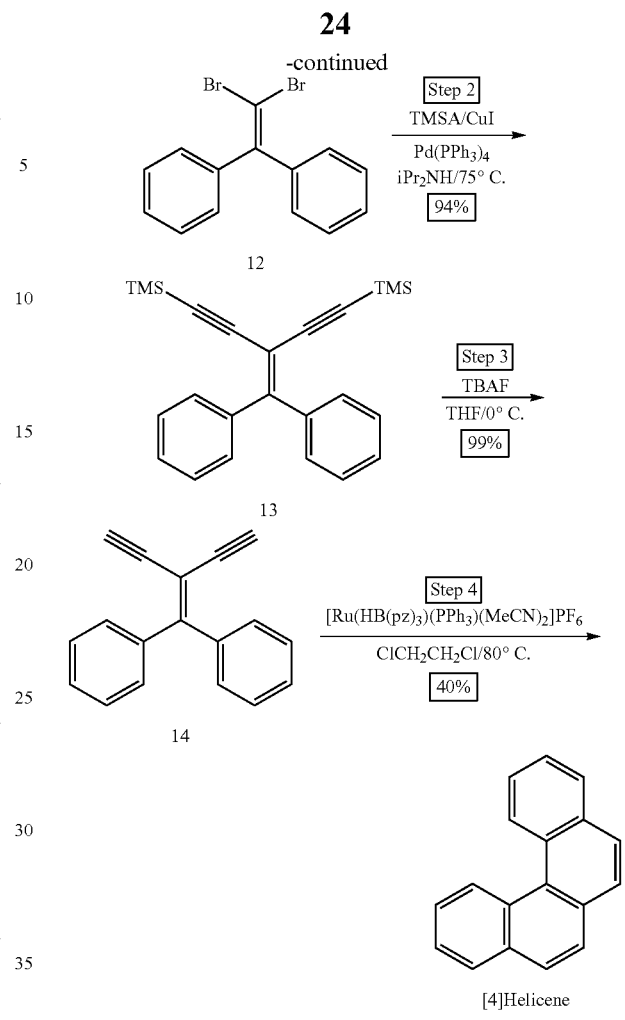

TMSA = trimethylsilylacetylene; pz = 1H-pyrazol-1-yl

[4]Helicene. [4]Helicene was prepared (Scheme 4) in four steps starting from benzo-phenone as previously described (Step 1, Step 2, Step 3, Step 4, and the preparation of [Ru(HB (pz)$_3$)(PPh$_3$)(MeCN)$_2$]PF$_6$) by using the following modifications to the original procedures: (1) The reaction conditions (PhMe, reflux, 24 h) were applied in Step 1. Product 12 was obtained in 64% yield. (See, Donovan, P. M.; Scott, L. T. *J. Am. Chem. Soc.* 2004, 126, 3108-3112; Shen, H.-C.; Tang, J.-M.; Chang, H. K.; Yang, C.-W.; Liu, R. S. *J. Org. Chem.* 2005, 70, 10113-10116 and Chan, W.-C.; Lau, C.-P.; Chen, Y.-Z.; Fang, Y.-Q.; Ng, S.-M. *Organometallics* 1997, 16, 34-44.) (2) The reaction conditions (TMSA (3 equiv), Pd(PPh$_3$)$_4$ (5%), CuI (10%), iPr$_2$NH, 75° C., 52 h) were applied in Step 2. Product 13 was obtained in (94%) yield. (3) Product 14 was obtained as a pale yellow solid in 99% yield. (4) The reaction conditions ([Ru(HB(pz)$_3$)(PPh$_3$)(MeCN)$_2$] PF$_6$ (3.4%), 48 h) were applied in Step 4. [4]Helicene was obtained in 40% yield.

Section C. Crystallographic Characterization

1) ExBox•4PF$_6$ a) Methods. ExBox•4PF$_6$ (3.0 mg, 2.4 μmol) was dissolved in MeCN (0.8 mL) and the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the solution of ExBox•4PF$_6$ in MeCN (3.0 mM) over the course of one week yielded colorless single crystals of ExBox•4PF$_6$.

The structure of ExBox•4PF$_6$ is shown in FIG. 6A-D. FIGS. 6A, 6B, 6C, and 6D show the top, side, a-axis, and b-axis views, respectively. Data were collected at 100 K on a Bruker Kappa APEX CCD Diffractometer equipped with a CuK$_\alpha$ microsource with Quazar optics.

b) Crystal Parameters. [C$_{48}$H$_{40}$N$_4$(PF$_6$)$_4$](MeCN)$_3$. Colorless block (0.13×0.12×0.11 mm). Monoclinic, C2/c, a=21.920(6), b=16.300(5), c=36.904(11) Å, α=90.000, β=98.513(2), γ=90.000°, V=13040.3(7) Å$^3$, Z=8, T=100(2) K, ρ$_{calc}$=1.402 g cm$^{-3}$, μ=2.059 mm$^{-1}$. Of a total of 52258 reflections which were collected, 10885 were unique (R$_{int}$=0.0477). Final R$_1$(F$^2$>2σF$^2$)=0.0825 and wR$_2$=0.2283. The structure was solved by direct methods and expanded using Fourier techniques. (Sheldrick, G. M. SHELXTL Version 6.14; Bruker Analytical X-Ray Instruments, Inc.: Madison, Wis., 2003.) Disordered PF$_6^-$ molecules were refined with similarity restraints on PF and FF distances to keep geometries reasonable, as well as with rigid bond and similar restraints to keep displacement parameters reasonable. CCDC Number: 893549.

2) ExBox ⊂ Azulene•4PF$_6$(Azulene)

a) Methods. Solid Azulene (0.34 mg, 2.7 μmol) was added to a solution of ExBox•4PF$_6$ in MeCN (3.0 mM, 0.8 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of Azulene and ExBox•4PF$_6$ in MeCN over the period of 3 d yielded gold single crystals of ExBox ⊂ Azulene•4PF$_6$(Azulene). Data were collected at 100 K on a Bruker Kappa APEX CCD Diffractometer equipped with a CuK$_\alpha$ microsource with MX optics.

b) Crystal Parameters. [C$_{48}$H$_{40}$N$_4$ ⊂ C$_{10}$H$_8$•(PF$_6$)$_4$](C$_{10}$H$_8$)(MeCN)$_3$. Gold block (0.33×0.24×0.14 mm). Triclinic, P-1, a=10.090(3), b=11.382(3), c=18.082(5) Å, α=71.694(10), β=79.448(10), γ=65.810(10)°, V=1794.77(9) Å$^3$, Z=1, T=100(2) K, ρ$_{calc}$=1.510 g cm$^{-3}$, μ=1.971 mm$^{-1}$. Of a total of 43173 reflections which were collected, 6433 were unique (R$_{int}$=0.0233). Final R$_1$(F$^2$>2σF$^2$)=0.0543 and wR$_2$=0.1456. The structure was solved by direct methods and expanded using Fourier techniques. (Sheldrick, G. M. SHELXTL Version 6.14; Bruker Analytical X-Ray Instruments, Inc.: Madison, Wis., 2003.) The two Azulene molecules were disordered over symmetry positions and refined with PART-1 commands. The 1,2 C—C distances were refined with similarity restraints (SADI) as well as the 1,3 distances for the seven-membered ring carbons only. Each Azulene was subjected to a flat restraint and displacement parameters for the carbon atoms were subjected to rigid bond (DELU) and similarity (SIMU) restraints. The disordered PF$_6^-$ anions were refined with SADI restraints to regularize the environment around each P atom, and with rigid bond and similarity restraints on all atoms. The NC, NMe, and CC bond distances on the MeCN molecules were refined with similarity restraints (SADI). All atoms of the disordered MeCN molecule were refined with global anisotropic displacement parameters. CCDC Number: 893550.

3) ExBox ⊂ Anthracene•4PF$_6$(Anthracene)

a) Methods. Solid Anthracene (0.52 mg, 2.9 μmol) was added to a solution of ExBox•4PF$_6$ in MeCN (3.0 mM, 0.9 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of Anthracene and ExBox•4PF$_6$ in MeCN over the period of 2 d yielded red single crystals of ExBox ⊂ Anthracene•4PF$_6$(Anthracene). Data were collected at 100 K on a Bruker Kappa APEX CCD Diffractometer equipped with a CuK$_c$ microsource with MX optics.

b) Crystal Parameters. [C$_{48}$H$_{40}$N$_4$ ⊂ C$_{14}$H$_{10}$•(PF$_6$)$_4$]•(C$_{14}$H$_{10}$)•(MeCN)$_2$. Red block (0.11×0.05×0.05 mm). Monoclinic, P2/c, a=11.174(3), b=18.965(5), c=33.876(8) Å, α=90.000, β=90.818(10), γ=90.000°, V=7177.8(3) Å$^3$, Z=4, T=100(2) K, ρ$_{calc}$=1.565 g cm$^{-3}$, μ=1.992 mm$^{-1}$. Of a total of 64930 reflections which were collected, 12907 were unique (R$_{int}$=0.0427). Final R$_1$(F$^2$>2σF$^2$)=0.0383 and wR$_2$=0.0954. The structure was solved by direct methods and expanded using Fourier techniques. (Sheldrick, G. M. SHELXTL Version 6.14; Bruker Analytical X-Ray Instruments, Inc.: Madison, Wis., 2003.) CCDC Number: 893551.

4) ExBox ⊂ Phenanthrene•4PF$_6$(Phenanthrene)

a) Methods. Solid Phenanthrene (0.52 mg, 2.9 μmol) was added to a solution of ExBox•4PF$_6$ in MeCN (3.0 mM, 0.9 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of Phenanthrene and ExBox•4PF$_6$ in MeCN over the period of 2 d yielded yellow single crystals of ExBox ⊂ Phenanthrene•4PF$_6$(Phenanthrene). Data were collected at 100 K on a Bruker Kappa APEX CCD Diffractometer equipped with a CuK$_n$ microsource with Quazar optics.

b) Crystal Parameters. [C$_{48}$H$_{40}$N$_4$ ⊂ C$_{14}$H$_{10}$•(PF$_6$)$_4$]•(C$_{14}$H$_{10}$)•(MeCN)$_2$. Yellow block (0.37×0.12×0.09 mm). Monoclinic, C2/c, a=11.247(7), b=19.121(13), c=33.700(2) Å, α=90.000, β=90.897(14), γ=90.000°, V=7246(8) Å$^3$, Z=4, T=100(2) K, ρ$_{calc}$=1.550 g cm$^{-3}$, μ=1.973 mm$^{-1}$. Of a total of 16633 reflections which were collected, 5949 were unique (R$_{int}$=0.0227). Final R$_1$(F$^2$>2σF$^2$)=0.0503 and wR$_2$=0.1328. The structure was solved by direct methods and expanded using Fourier techniques. (Sheldrick, G. M. SHELXTL Version 6.14; Bruker Analytical X-Ray Instruments, Inc.: Madison, Wis., 2003.) A group anisotropic displacement parameter was refined for the disordered Phenanthrene. Distances were also restrained for the disordered Phenanthrene. CCDC Number: 893552.

5) ExBox ⊂ Pyrene•4PF$_6$(Pyrene)

a) Methods. Solid Pyrene (0.67 mg, 3.3 μmol) was added to a solution of ExBox•4PF$_6$ in MeCN (3.0 mM, 1 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of Pyrene and ExBox•4PF$_6$ in MeCN over the period of 3 d yielded orange single crystals of ExBox ⊂ Pyrene•4PF$_6$(Pyrene). Data were collected at 100 K on a Bruker Kappa APEX CCD Diffractometer equipped with a CuK$_\alpha$ microsource with Quazar optics.

b) Crystal Parameters. [C$_{48}$H$_{40}$N$_4$ ⊂ C$_{16}$H$_{10}$•(PF$_6$)$_4$]•(C$_{16}$H$_{10}$)•(MeCN)$_2$. Orange block (0.30×0.14×0.14 mm). Triclinic, P-1, a=9.926(3), b=10.725(4), c=18.056(6) Å, α=97.803(10), β=91.899(10), γγ=103.705(10)°, V=1845.73(11) Å$^3$, Z=1, T=100(2) K, ρ$_{calc}$=1.565 g cm$^{-3}$, μ=1.956 mm$^{-1}$. Of a total of 28734 reflections which were collected, 6520 were unique (R$_{int}$=0.0331). Final R$_1$(F$^2$>2σF$^2$)=0.025 and wR$_2$=0.0895. The structure was solved by direct methods and expanded using Fourier techniques. (Sheldrick, G. M. SHELXTL Version 6.14; Bruker Analytical X-Ray Instruments, Inc.: Madison, Wis., 2003.) CCDC Number: 893553.

6) ExBox ⊂ Tetracene•4PF$_6$ a) Methods. A mixture of Tetracene (0.30 mg, 1.3 μmol), ExBox•4PF$_6$ (1.5 mg, 1.2 μmol), MeCN (0.8 mL), and PhMe (0.8 mL) was heated at 100° C. for 30 min before an additional portion of MeCN (0.8 mL) was added. The resulting solution was then allowed to slowly cool to room temperature and was passed through a 0.45 μm filter equally into three 1 mL tubes. The tubes were placed together in one 20 mL vial containing iPr$_2$O (~1.5 mL) and the vial was capped. Slow vapor diffusion of iPr$_2$O into the 1.1:1 solution of Tetracene and ExBox•4PF$_6$ in MeCN/PhMe over the period of 3 d yielded red single crystals of ExBox ⊂ Tetracene•4PF$_6$. Data were collected at 100 K on a Bruker Kappa APEX2 CCD Diffractometer equipped with a CuK$_α$, microsource with Quazar optics. Note the chemical formula in the Crystal Parameters section below reflects that only half of the total number of ExBox•4PF$_6$ cyclophanes in the crystal are occupied with Tetracene molecules.

b) Crystal Parameters. [C$_{48}$H$_{40}$N$_4$ ⊂ (C$_{18}$H$_{12}$)$_{0.5}$•(PF$_6$)$_4$]•(C$_7$H$_8$)$_2$•(MeCN)$_2$. Red block (0.47×0.16×0.07 mm). Triclinic, P-1, a=10.140(3), b=11.252(3), c=17.944(5) Å, α=72.280(17), β=86.535(17), γ=65.818(15)°, V=1774.21(9) Å$^3$, Z=1, T=105.4(2) K, ρ$_{calc}$=1.529 g cm$^{-3}$, μ=1.989 mm$^{-1}$. Of a total of 9607 reflections which were collected, 5636 were unique (R$_{int}$=0.0180). Final R$_1$(F$^2$>2σF$^2$)=0.0647 and wR$_2$=0.1766. The structure was solved by direct methods and expanded using Fourier techniques. (Sheldrick, G. M. SHELXTL Version 6.14; Bruker Analytical X-Ray Instruments, Inc.: Madison, Wis., 2003.) Rigid bond restraints were imposed on the displacement parameters as well as restraints on similar amplitudes separated by less than 1.7 Å on the disordered PhMe and PF6 molecules. Distance restraints were refined for the disordered PF6 molecules and an idealized six-membered ring was constrained for the disordered PhMe molecule. CCDC Number: 893554.

7) ExBox ⊂ Tetraphene•4PF$_6$ a) Methods. Solid Tetraphene (0.60 mg, 2.6 μmol) was added to a solution of ExBox•4PF$_6$ in MeCN (3.0 mM, 0.8 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of Tetraphene and ExBox•4PF$_6$ in MeCN over the period of 2 d yielded orange single crystals of ExBox ⊂ Tetraphene•4PF$_6$. Data were collected at 100 K on a Bruker Kappa APEX CCD Diffractometer equipped with a CuK$_n$ microsource with Quazar optics. Note the chemical formula in the Crystal Parameters section below reflects that only half of the total number of ExBox•4PF$_6$ cyclophanes in the crystal are occupied with Tetraphene molecules.

b) Crystal Parameters. [C$_{48}$H$_{40}$N$_4$ ⊂ (C$_{18}$H$_{12}$)$_{0.5}$•(PF$_6$)$_4$]•(MeCN)$_3$. Orange block (0.76×0.22×0.12 mm). Triclinic, P-1, a=10.143(4), b=11.110(4), c=17.953(7) Å, α=74.054(2), β=84.440(2), γ=64.486(2)°, V=1754.90(12) Å$^3$, Z=1, T=100(2) K, ρ$_{calc}$=1.410 g cm$^{-3}$, μ=1.959 mm$^{-1}$. Of a total of 19182 reflections which were collected, 5682 were unique (R$_{int}$=0.0407). Final R$_1$(F$^2$>2σF$^2$)=0.1085 and wR$_2$=0.3481. The structure was solved by direct methods and expanded using Fourier techniques. (Sheldrick, G. M. SHELXTL Version 6.14; Bruker Analytical X-Ray Instruments, Inc.: Madison, Wis., 2003.) Rigid bond restraints (esd 0.01) were imposed on the displacement parameters as well as restraints on similar amplitudes (esd 0.05) separated by less than 1.7 Å on the disordered fluorine atoms. A group anisotropic displacement parameter was refined for the disordered Tetraphene molecule. CCDC Number: 893555.

8) ExBox ⊂ Chrysene•4PF$_6$ a) Methods. Solid Chrysene (0.60 mg, 2.6 μmol) was added to a solution of ExBox•4PF$_6$ in MeCN (3.0 mM, 0.8 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of Chrysene and ExBox•4PF$_6$ in MeCN over the period of 3 d yielded orange single crystals of ExBox ⊂ Chrysene•4PF$_6$. Data were collected at 100 K on a Bruker Kappa APEX CCD Diffractometer equipped with a MoK$_α$ sealed tube with graphite.

b) Crystal Parameters. [C$_{48}$H$_{40}$N$_4$ ⊂ (C$_{18}$H$_{12}$)•(PF$_6$)$_4$]•(MeCN)$_6$. Orange block (0.58×0.33×0.17 mm). Monoclinic, P21/n, a=11.017(5), b=14.579(7), c=24.259(7) Å, α=90.000, β=98.998(2), γ=90.000°, V=3848.5(3) Å$^3$, Z=2, T=100(2) K, ρ$_{calc}$=1.491 g cm$^{-3}$, μ=0.209 mm$^{-1}$. Of a total of 83941 reflections which were collected, 11236 were unique (R$_{int}$=0.1244). Final R$_1$(F$^2$>2σF$^2$)=0.0825 and wR$_2$=0.1886. The structure was solved by direct methods and expanded using Fourier techniques. (Sheldrick, G. M. SHELXTL Version 6.14; Bruker Analytical X-Ray Instruments, Inc.: Madison, Wis., 2003.) CCDC Number: 893556.

9) ExBox ⊂ [4]Helicene•4PF$_6$ a) Methods. Solid [4]Helicene (0.60 mg, 2.6 μmol) was added to a solution of ExBox•4PF$_6$ in MeCN (3.0 mM, 0.8 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of [4]Helicene and ExBox•4PF$_6$ in MeCN over the period of 3 d yielded yellow single crystals of ExBox ⊂ [4]Helicene•4PF$_6$. Data were collected at 100 K on a Bruker Kappa APEX2 CCD Diffractometer equipped with a CuIc microsource with Quazar optics.

b) Crystal Parameters. [C$_{48}$H$_{40}$N$_4$ ⊂ (C$_{18}$H$_{12}$)•(PF$_6$)$_4$]•(MeCN)$_2$. Yellow block (0.11×0.08×0.02 mm). Triclinic, P-1, a=10.561(6), b=11.101(6), c=18.025(11) Å, α=72.955, β=82.376(2), γ=63.569°, V=1809.2(18) Å$^3$, Z=1, T=220(2) K, ρ$_{calc}$=1.417 g cm$^{-3}$, μ=1.918 mm$^{-1}$. Of a total of 9232 reflections which were collected, 5453 were unique (R$_{int}$=0.0343). Final R$_1$(F$^2$>2σF$^2$)=0.1247 and wR$_2$=0.3582. The structure was solved by direct methods and expanded using Fourier techniques. (Sheldrick, G. M. SHELXTL Version 6.14; Bruker Analytical X-Ray Instruments, Inc.: Madison, Wis., 2003.) Rigid bond restraints (esd 0.01) were imposed on the displacement parameters as well as restraints on similar amplitudes (esd 0.05) separated by less than 1.7 Å on the disordered fluorine and [4]Helicene atoms. Distance restraints were imposed on the [4]Helicene molecule. CCDC Number: 893557.

10) ExBox ⊂ Triphenylene•4PF$_6$ a) Methods. Solid Triphenylene (0.60 mg, 2.6 μmol) was added to a solution of ExBox•4PF$_6$ in MeCN (3.0 mM, 0.8 mL) and, after it dissolved, the mixture was passed through a 0.45 μm filter equally into three 1 mL tubes. The tubes were placed together in one 20 mL vial containing iPr$_2$O (~3 mL) and the vial was capped. Slow vapor diffusion of iPr$_2$O into the 1.1:1 solution of Triphenylene and ExBox•4PF$_6$ in MeCN over the period of 3 d yielded yellow single crystals of ExBox ⊂ Triphenylene•4PF$_6$. Data were collected at 100 K on a Bruker Kappa APEX CCD Diffractometer equipped with a MoK$_n$ sealed tube with graphite.

b) Crystal Parameters. [C$_{48}$H$_{40}$N$_4$ ⊂ (C$_{18}$H$_{12}$)•(PF$_6$)$_4$]•(MeCN)$_3$. Yellow block (0.35×0.21×0.04 mm). Triclinic, P-1, a=10.019(12), b=10.770(13), c=18.071(2) Å, α=73.537(6), β=74.926(6), γ=70.374(4)°, V=1731.9(4) Å$^3$, Z=1, T=100(2) K, ρ$_{calc}$=1.538 g cm$^{-3}$, μ=0.224 mm$^{-1}$. Of a total of 20831 reflections which were collected, 7170 were unique (R$_{int}$=0.1272). Final R$_1$(F$^2$>2σF$^2$)=0.0991 and wR$_2$=0.2832. The structure was solved by direct methods and expanded using Fourier techniques. (Sheldrick, G. M. SHELXTL Version 6.14; Bruker Analytical X-Ray Instruments, Inc.: Madison, Wis., 2003.) Rigid bond restraints (esd 0.01) were imposed on the displacement parameters as well as restraints on similar amplitudes separated by less than 1.7 Å on the disordered fluorine (esd 0.02), Triphenylene, and MeCN (esd 0.01) molecules. Similar distance restraints were also restrained for the disordered $PF_6$ Triphenylene, and MeCN molecules. CCDC Number: 893558.

11) ExBox ⊂ Perylene•$4PF_6$ a) Methods. Solid Perylene (0.74 mg, 2.9 μmol) was added to a solution of ExBox•$4PF_6$ in MeCN (3.0 mM, 0.9 mL) and, after it dissolved, the mixture was passed through a 0.45 μm filter equally into three 1 mL tubes. The tubes were placed together in one 20 mL vial containing $iPr_2O$ (~3 mL) and the vial was capped. Slow vapor diffusion of $iPr_2O$ into the 1.1:1 solution of Perylene and ExBox•$4PF_6$ in MeCN over the period of 2 d yielded red single crystals of ExBox ⊂ Perylene•$4PF_6$. Data were collected at 100 K on a Bruker Kappa APEX CCD Diffractometer equipped with a $CuK_\alpha$ microsource with Quazar optics.

b) Crystal Parameters. $[C_{48}H_{40}N_4 \subset (C_{20}H_{12})\bullet(PF_6)_4]\bullet(MeCN)_7$. Red block (0.59×0.44×0.33 mm). Monoclinic, P21/c, a=20.957(5), b=17.985(5), c=22.883(6) Å, α=90.000, β=107.919(10), γ=90.000°, V=8206.5(4) Å$^3$, Z=4, T=100(2) K, $\rho_{calc}$=1.451 g cm$^{-3}$, μ=1.793 mm$^{-1}$. Of a total of 53076 reflections which were collected, 13781 were unique ($R_{int}$=0.0224). Final $R_1(F^2>2\sigma F^2)$=0.0645 and $wR_2$=0.1675. The structure was solved by direct methods and expanded using Fourier techniques. (Sheldrick, G. M. SHELXTL Version 6.14; Bruker Analytical X-Ray Instruments, Inc.: Madison, Wis., 2003.) Rigid bond restraints (esd 0.01) were imposed on the displacement parameters as well as restraints on similar amplitudes (esd 0.05) separated by less than 1.7 Å on the disordered fluorine and carbon atoms. CCDC Number: 893559.

12) ExBox ⊂ Coronene•$4PF_6$ a) Methods. Solid Coronene (0.88 mg, 2.9 μmol) was added to a solution of ExBox•$4PF_6$ in MeCN (3.0 mM, 0.9 mL) and, after it dissolved, the mixture was passed through a 0.45 μm filter equally into three 1 mL tubes. The tubes were placed together in one 20 mL vial containing $iPr_2O$ (~3 mL) and the vial was capped. Slow vapor diffusion of $iPr_2O$ into the 1.1:1 solution of Coronene and ExBox•$4PF_6$ in MeCN over the period of 2 d yielded orange single crystals of ExBox ⊂ Coronene•$4PF_6$. Data were collected at 100 K on a Bruker Kappa APEX CCD Diffractometer equipped with a $MoK_\alpha$ microsource with Quazar optics.

b) Crystal Parameters. $[C_{48}H_{40}N_4 \subset (C_{24}H_{12})\bullet(PF_6)_4]\bullet(MeCN)_7$. Orange block (0.46×0.30×0.09 mm). Triclinic, P-1, a=10.573(6), b=14.317(7), c=14.733(8) Å, α=102.508(3), β=93.376(3), γ=109.336(3)°, V=2033.67(19) Å$^3$, Z=1, T=100(2) K, $\rho_{calc}$=1.503 g cm$^{-3}$, μ=0.203 mm$^{-1}$. Of a total of 23957 reflections which were collected, 11913 were unique ($R_{int}$=0.0662). Final $R_1(F^2>2\sigma F^2)$=0.0459 and $wR_2$=0.0832. The structure was solved by direct methods and expanded using Fourier techniques. (Sheldrick, G. M. SHELXTL Version 6.14; Bruker Analytical X-Ray Instruments, Inc.: Madison, Wis., 2003.) Rigid bond restraints (esd 0.01) were imposed on the displacement parameters as well as restraints on similar amplitudes (esd 0.05) separated by less than 1.7 Å on the disordered fluorine atoms and MeCN molecules. CCDC Number: 893560.

Section D. Spectroscopic and Spectrometric Characterizations

ExBox•$4PF_6$ and its Complexes a) UV/Vis Absorption Spectra

Optical absorption spectra (all at 0.5 mM, 298 K) were obtained for (i) the PAH guests (in MeCN or $CHCl_3$/MeCN (1:1) depending on solubility), (ii) ExBox$^{4+}$ (in MeCN), and (iii) the corresponding 1:1 complexes (in MeCN), with the exception of Tetracene because of issues with solubility (heating to 100° C. is required to solubilize Tetracene in PhMe). Heating the 1:1 mixture of host and guest would, however, inevitably lead to a much lower binding affinity. The data reflects the emergence of a new charge-transfer band ranging from 350 to 600 nm for all of the 1:1 complexes studied, except for Azulene, which showed no noticeable shifting of the bands when the host and guest were combined.

b) $^1$H NMR/$^{13}$C NMR Spectroscopic Analysis $^1$H NMR (298 K, 500 MHz) titrations were performed by adding small volumes of a concentrated guest solution/suspension in $CDCl_3$ to a solution of ExBox$^{4+}$ in $CD_3CN$. Tetramethylsilane (TMS) was used as a reference. Significant upfield shifts of the $^1$H resonances for γ protons were observed and used to determine the association constants ($K_a$). The $K_a$ values were calculated using Dynafit, a program which employs nonlinear least-squares regression on ligand—receptor binding data. (See, Kuzmic, P. *Anal. Biochem.* 1996, 237, 260-273.) In the case of 10 and 11, the low solubility of Perylene and Coronene prohibited the calculation of reliable $K_a$ values. The estimated $K_a$ value for 10 is reported, however, the error is substantial (76%).

Isothermal Titration Calorimetry (ITC)

All ITC measurements were performed in dry, degassed MeCN at 298 K. A solution of ExBox$^{4+}$ (in MeCN) was used as the host solution in a 1.8 mL cell. Solutions of aromatic guests (in MeCN) were added by successively injecting 10 μL of titrant over 20 s (25×) with a 300 s interval between each injection. Experiments were repeated three times. Thermodynamic information was calculated using a one-site binding model utilizing data from which the heat of dilution of the guest was subtracted, with the average of three runs reported.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A cyclophane of formula I:

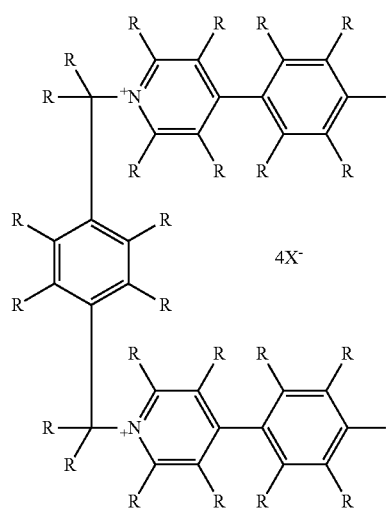

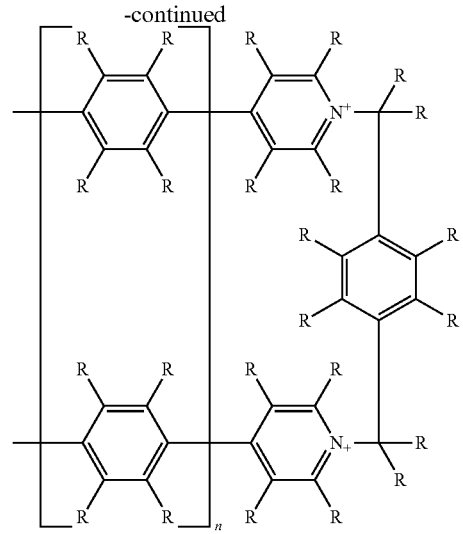

wherein n≥0; R is independently selected from the group consisting of H, alkyl groups, alkenyl groups, alkynyl groups, aryl groups, alkoxy groups, OH, $NH_2$, SH, F, Cl, Br, I, $P(R_1)_2$, CHO, $COOR_1$, COOM, $CH_2OR_1$, $CH_2OM$, $OR_1$, $NHCOR_1$, $CONHR_1$, CONHM, $CON(R_1)_2$, $N_3$, $NO_2$, $B(OR_1)_2$, $B(OM)_2$, CN, $N(R_1)^{3+}$, $P(R_1)^{3+}$, $PO(R_1)_2$, and OM, where $R_1$ is independently selected from the group consisting of H, alkyl groups, alkenyl groups, alkynyl groups, and aryl groups and M is independently selected from the group consisting of Li, Na, K, Rb and Cs; and $X^-$ is an organic or inorganic negatively charged ion.

2. The cyclophane of claim 1, wherein n is 0.

3. The cyclophane of claim 2, wherein all R groups are H atoms.

4. A cyclophane of formula I:

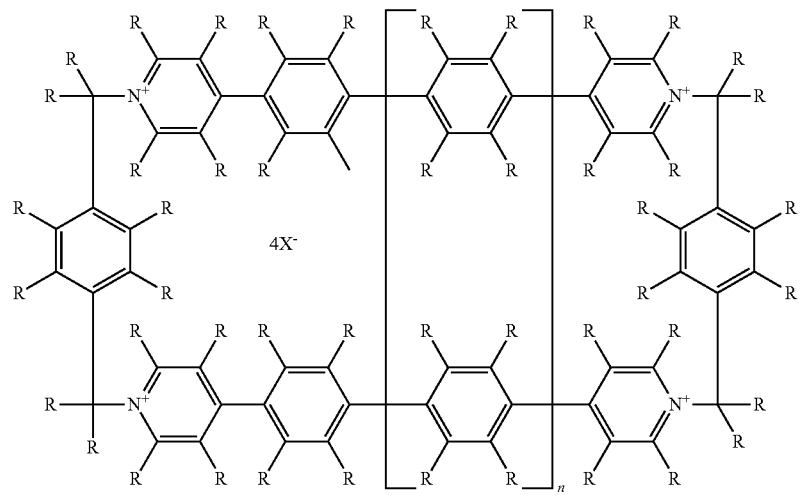

wherein n is 1; R is independently selected from the group consisting of H, alkyl groups, alkenyl groups, alkynyl groups, aryl groups, alkoxy groups, OH, $NH_2$, SH, F, Cl, Br, I, $P(R_1)_2$, CHO, $COOR_1$, COOM, $CH_2OR_1$, $CH_2OM$, $OR_1$, $NHCOR_1$, $CONHR_1$, CONHM, $CON(R_1)_2$, $N_3$, $NO_2$, $B(OR_1)_2$, $B(OM)_2$, CN, $N(R_1)^{3+}$, $P(R_1)^{3+}$, $PO(R_1)_2$, and OM, where $R_1$ is independently selected from the group consisting of H, alkyl groups, alkenyl groups, alkynyl groups, and aryl groups and M is independently selected from the group consisting of Li, Na, K, Rb and Cs; and $X^-$ is an organic or inorganic negatively charged ion.

5. The cyclophane of claim 4, wherein all R groups are H atoms.

6. A cyclophane of formula I:

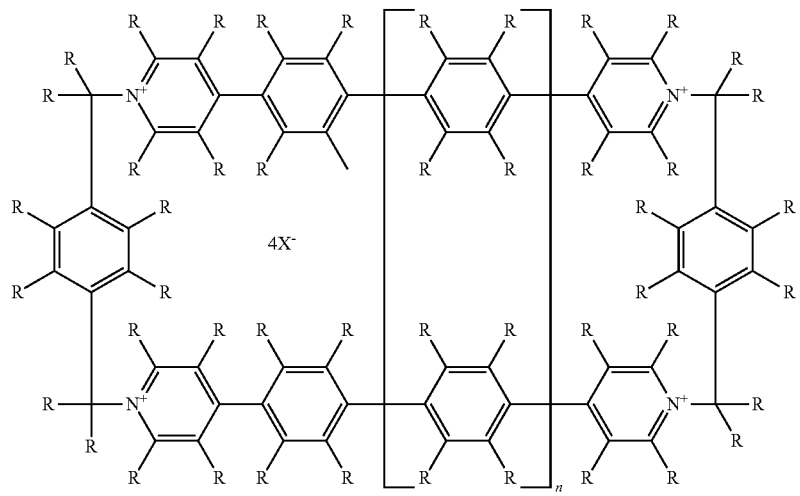

wherein n is greater than or equal to 2; R is independently selected from the group consisting of H, alkyl groups, alkenyl groups, alkynyl groups, aryl groups, alkoxy groups, OH, $NH_2$, SH, F, Cl, Br, I, $P(R_1)_2$, CHO, $COOR_1$, COOM, $CH_2OR_1$, $CH_2OM$, $OR_1$, $NHCOR_1$, $CONHR_1$, CONHM, $CON(R_1)_2$, $N_3$, $NO_2$, $B(OR_1)_2$, $B(OM)_2$, CN, $N(R_1)^{3+}$, $P(R_1)^{3+}$, $PO(R_1)_2$ and OM, where $R_1$ is independently selected from the group consisting of H, alkyl groups, alkenyl groups, alkynyl groups, and aryl groups and M is independently selected from the group consisting of Li, Na, K, Rb and Cs; and $X^-$ is an organic or inorganic negatively charged ion.

7. A method of sequestering polyaromatic hydrocarbons from a sample comprising polyaromatic hydrocarbons, the method comprising mixing one or more of the cyclophanes of claim 1 with the sample, whereby the polyaromatic hydrocarbons form an inclusion complex with the cyclophanes.

8. The method of claim 7, further comprising removing the cyclophanes and their complexed polyaromatic hydrocarbons from the sample and subsequently separating the complexed polyaromatic hydrocarbons from the cyclophanes.

9. The method of claim 7, wherein the sample comprises an organic liquid.

10. The method of claim 9, wherein the organic liquid comprises crude oil.

11. The method of claim 7, wherein the sample is an aqueous liquid sample.

12. The method of claim 11, wherein the aqueous liquid sample comprises drinking water or water from a natural body of water.

13. The method of claim 7, wherein the sample is a vapor phase sample.

14. The method of claim 13, wherein the vapor phase sample comprises an exhaust stream from a vehicle, cigarette smoke or exhaust from an industrial manufacturing facility.

15. A chromatographic method of separating polyaromatic hydrocarbons in a sample comprising more than one type of polyaromatic hydrocarbon, the method comprising passing the sample over a solid support material on which one or more of the cyclophanes of claim 1 are immobilized, whereby the polyaromatic hydrocarbons undergo reversible electron donor-acceptor complexation and dissociation interactions with the polyaromatic hydrocarbons, such that different types of the polyaromatic hydrocarbons are separated from one another as they pass over the solid support material.

16. A method for detecting the presence of polyaromatic hydrocarbons in a sample, the method comprising mixing one or more of the cyclophanes of claim 1 with the sample, whereby the polyaromatic hydrocarbons form inclusion complexes with the cyclophanes and produce a visible color change in the sample; and monitoring the color change.

17. A method of exfoliating graphene nanoribbons in multi-layered graphene nanoribbon stack, the method comprising exposing the multi-layered graphene nanoribbon stack to a solution comprising one or more of the cyclophanes of claim 1, whereby the cyclophanes form polypseudorotaxanes with the graphene nanoribbons which results in the exfoliation of individual nanoribbons as the result of Coulombic repulsion between the cyclophanes.

18. The method of claim 17, wherein the step of exposing the multi-layered graphene nanoribbon stack to the cyclophanes comprises synthesizing the graphene nanoribbon stack in the presence of the cyclophanes.

19. The method of claim 17, wherein the step of exposing the multi-layered graphene nanoribbon stack to the cyclophanes comprises adding the cyclophanes to a solution comprising the graphene nanoribbon stack, and agitating the solution.

* * * * *